(12) United States Patent
Okiyama

(10) Patent No.: US 9,795,736 B2
(45) Date of Patent: Oct. 24, 2017

(54) INFUSION SET AND METHOD FOR USING SAME

(71) Applicant: JMS CO., LTD., Hiroshima-shi, Hiroshima (JP)

(72) Inventor: Tadashi Okiyama, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 460 days.

(21) Appl. No.: 14/418,029

(22) PCT Filed: Jul. 31, 2013

(86) PCT No.: PCT/JP2013/070782
§ 371 (c)(1),
(2) Date: Jan. 28, 2015

(87) PCT Pub. No.: WO2014/021390
PCT Pub. Date: Feb. 6, 2014

(65) Prior Publication Data
US 2015/0297830 A1 Oct. 22, 2015

(30) Foreign Application Priority Data
Aug. 1, 2012 (JP) .................... 2012-171229

(51) Int. Cl.
*A61M 5/178* (2006.01)
*A61M 5/168* (2006.01)
(Continued)

(52) U.S. Cl.
CPC ........ *A61M 5/16813* (2013.01); *A61M 5/162* (2013.01); *A61M 39/10* (2013.01);
(Continued)

(58) Field of Classification Search
CPC .. A61M 2005/1402; A61M 2039/0009; A61M 2039/1016; A61M 2039/1027;
(Continued)

(56) References Cited

U.S. PATENT DOCUMENTS 5,330,235 A * 7/1994 Wagner ............... F16L 37/0985
285/320
5,385,372 A 1/1995 Utterberg
(Continued)

FOREIGN PATENT DOCUMENTS

EP 1 980 291 10/2008
EP 2 351 550 8/2011
(Continued)

OTHER PUBLICATIONS

Extended European Search Report issued in corresponding European Patent Application No. 13825662.3, dated Apr. 14, 2016 11 pages.
(Continued)

*Primary Examiner* — Rebecca E Eisenberg
(74) *Attorney, Agent, or Firm* — Hamre, Schumann, Mueller & Larson, P.C.

(57) ABSTRACT

An infusion set (1) includes a first flow channel (10) constituted by a pliable tube (10a) and including a spike (11) provided at one end thereof, a second flow channel (20) constituted by a pliable tube (20a) and including a lock connector (50) provided at one end thereof, the lock connector (50) including a lock mechanism (60) that is brought into engagement with a female connector (200), a third flow channel (30) constituted by pliable tubes (30a, 30b and 30c) and including a male connector (31) provided at one end thereof, and a three-way stopcock (40) to which another end of the first flow channel, another end of the second flow channel and another end of the third flow channel are connected. The three-way stopcock includes a handle (41) that can be switched between a first position that brings the first flow channel and the third flow channel into communication with each other and a second position that brings the
(Continued)

second flow channel and the third flow channel into communication with each other.

12 Claims, 13 Drawing Sheets

(51) Int. Cl.
*A61M 5/162* (2006.01)
*A61M 39/10* (2006.01)
*A61M 39/22* (2006.01)
*A61M 39/28* (2006.01)
*A61M 39/26* (2006.01)
*A61M 39/00* (2006.01)
*A61M 5/14* (2006.01)

(52) U.S. Cl.
CPC .......... *A61M 39/223* (2013.01); *A61M 39/26* (2013.01); *A61M 39/28* (2013.01); *A61M 39/285* (2013.01); *A61M 5/1408* (2013.01); *A61M 39/1011* (2013.01); *A61M 2005/1402* (2013.01); *A61M 2039/0009* (2013.01); *A61M 2039/1016* (2013.01); *A61M 2039/1027* (2013.01); *A61M 2039/1072* (2013.01); *A61M 2039/229* (2013.01); *A61M 2039/267* (2013.01)

(58) Field of Classification Search
CPC .... A61M 2039/1072; A61M 2039/229; A61M 2039/267; A61M 39/10; A61M 39/1011; A61M 39/223; A61M 39/26; A61M 39/28; A61M 39/285
See application file for complete search history.

(56) References Cited

U.S. PATENT DOCUMENTS

| | | | | |
|---|---|---|---|---|
| 5,496,274 | A | * | 3/1996 | Graves ............... A61M 39/1011 604/192 |
| 5,593,385 | A | * | 1/1997 | Harrison ............. A61M 5/1412 604/83 |
| 5,807,312 | A | * | 9/1998 | Dzwonkiewicz ... A61M 5/1424 604/248 |
| 6,468,251 | B1 | | 10/2002 | Yamanaka et al. |
| 6,485,483 | B1 | | 11/2002 | Fujii |
| 2003/0032940 | A1 | | 2/2003 | Doyle |
| 2005/0002806 | A1 | | 1/2005 | Fuechslin et al. |
| 2005/0151105 | A1 | | 7/2005 | Ryan et al. |
| 2005/0234428 | A1 | | 10/2005 | Spohn et al. |
| 2007/0161970 | A1 | | 7/2007 | Spohn et al. |
| 2009/0018513 | A1 | | 1/2009 | Fujii et al. |
| 2009/0143731 | A1 | | 6/2009 | Guzman |
| 2009/0326506 | A1 | | 12/2009 | Hasegawa et al. |
| 2011/0160679 | A1 | | 6/2011 | Okiyama et al. |

FOREIGN PATENT DOCUMENTS

| | | |
|---|---|---|
| JP | 61-145542 U | 9/1986 |
| JP | 3-88553 U | 9/1991 |
| JP | 3-504571 | 10/1991 |
| JP | 7-047137 | 2/1995 |
| JP | 9-500563 | 1/1997 |
| JP | 9-182791 | 7/1997 |
| JP | 3052751 U | 10/1998 |
| JP | 2000-350787 | 12/2000 |
| JP | 3389983 B | 3/2003 |
| JP | 2004-000483 | 1/2004 |
| JP | 2005-508712 | 4/2005 |
| JP | 2005-144063 | 6/2005 |
| JP | 2007-044562 | 2/2007 |
| JP | 2008-017987 | 1/2008 |
| JP | 201370832 Y | 12/2009 |
| JP | 2010-075684 | 4/2010 |
| JP | 4735646 B | 7/2011 |
| WO | 90/11103 | 10/1990 |
| WO | 95/03509 | 2/1995 |
| WO | 2006/037638 | 4/2006 |
| WO | 2006/060688 | 6/2006 |
| WO | 2007/148708 | 12/2007 |
| WO | 2011/156521 | 12/2011 |

OTHER PUBLICATIONS

Office Action issued in corresponding Japanese patent application, dated Oct. 20, 2016, 5 pages.

Office Action issued in corresponding Chinese Patent Application Serial No. 201380040565.6, dated Oct. 10, 2016, 7 pages.

* cited by examiner

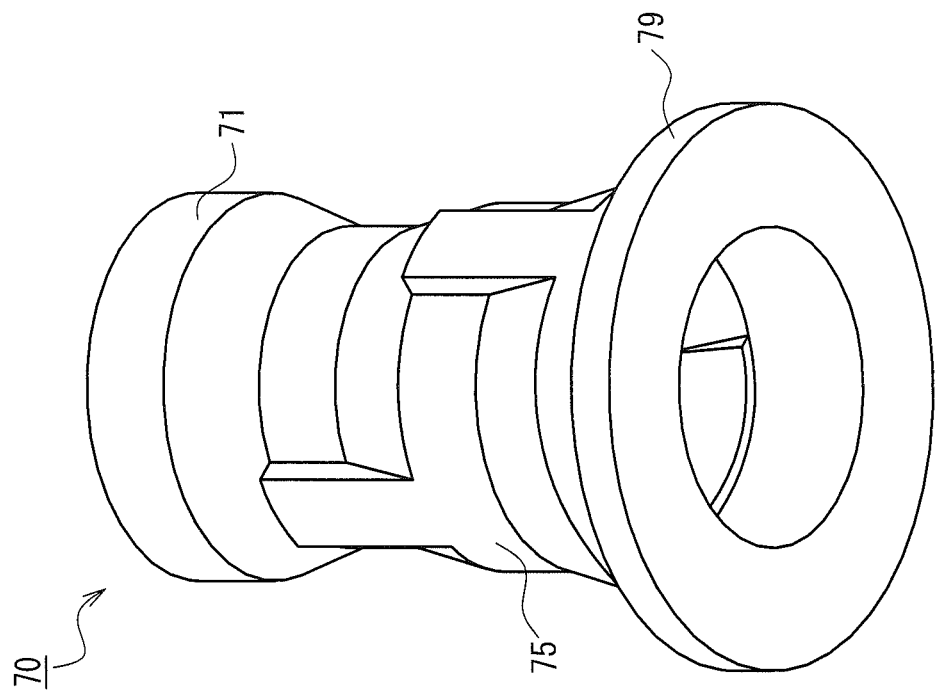
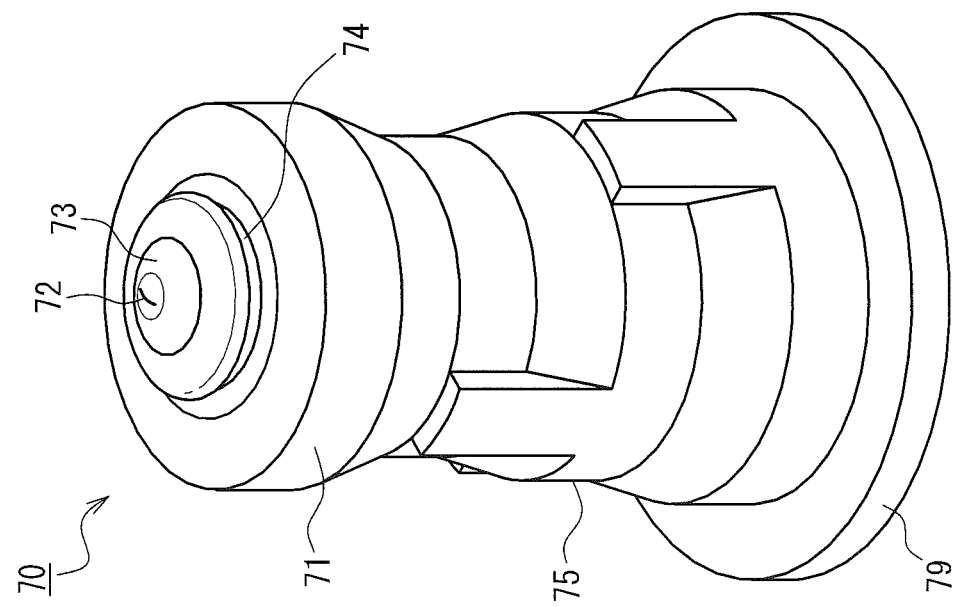

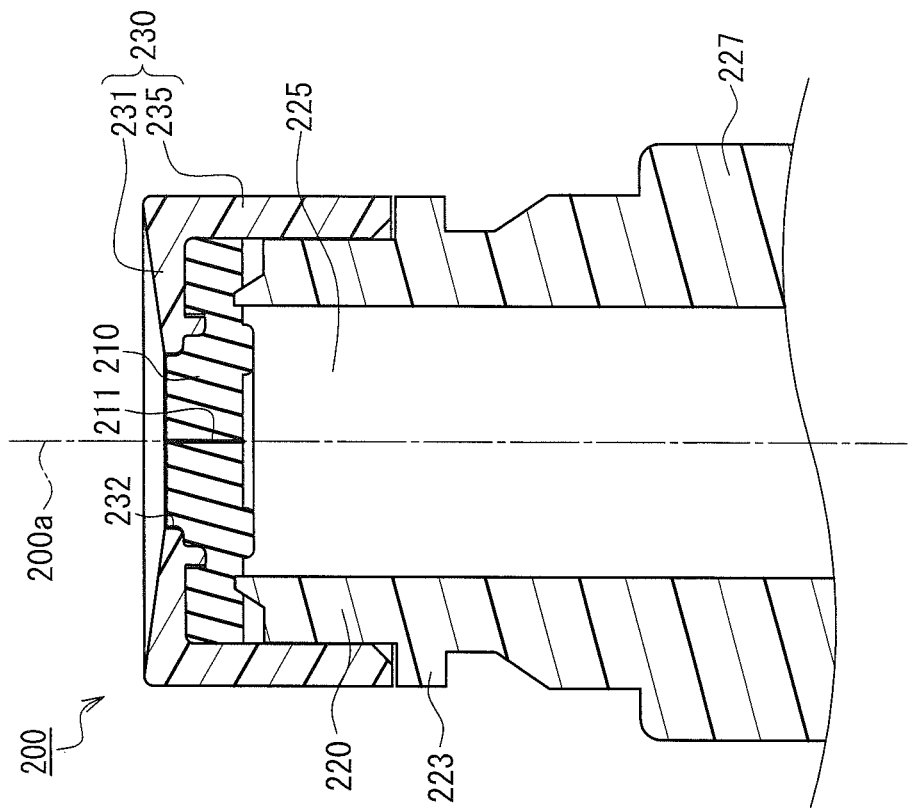
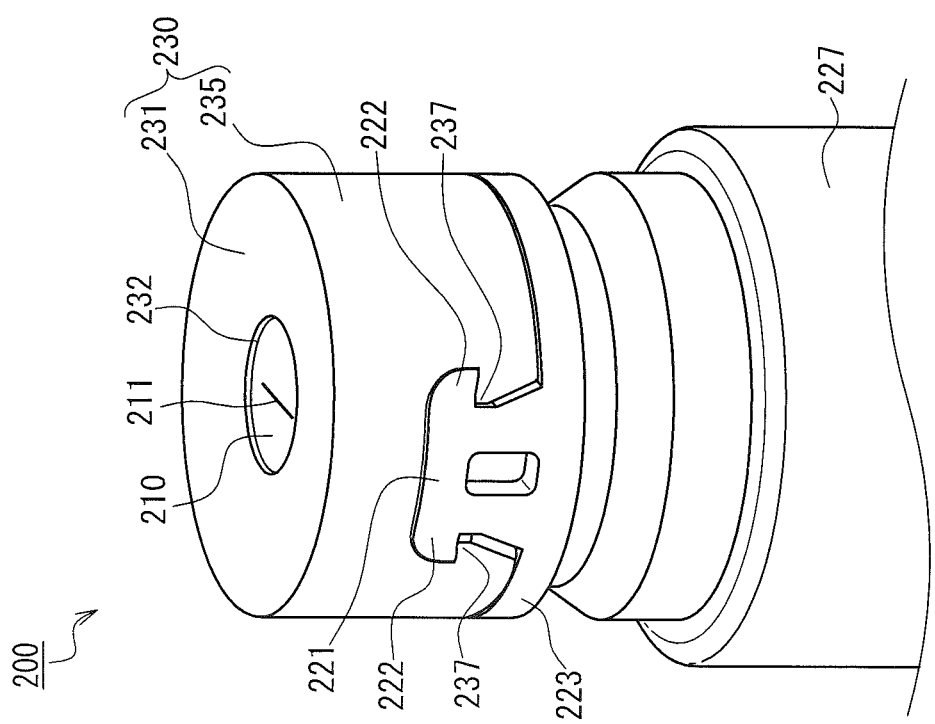

… (1)

INFUSION SET AND METHOD FOR USING SAME

TECHNICAL FIELD

The present invention relates to an infusion set used when administering a liquid such as a medical solution to a patient. The present invention also relates to a method for using the infusion set.

BACKGROUND ART

FIG. 13 is a diagram showing a schematic configuration of a conventional infusion set 100. The infusion set 100 includes a flow channel 110 through which a medical solution flows. The flow channel 110 is constituted by tubes 110a and 110b. A spike 111 is provided at an upstream end of the flow channel 110, and a male connector 112 is provided at a downstream end of the flow channel 110. The tube 110a and the tube 110b are in communication with each other via a drip chamber 113. A roller clip 114 and a pinch clamp 115 are provided along the tube 110b.

The spike 111 is inserted into a port of a medical solution bag in which a medical solution is stored. A downstream end of the male connector 112 is connected to an upstream end of a tube having a needle that is pierced into the vein of a patient. The drip chamber 113 allows visual observation of the medical solution flowing through the flow channel 110. The roller clip 114 allows the flow rate of the medical solution to be set as desired through adjustment of the cross sectional area of the medical solution flow channel of the tube 110b. The pinch clamp 115 has a function of opening and closing the medical solution flow channel of the tube 110b.

Administration of a medical solution using the infusion set 100 having the above-described configuration is performed in the following manner.

The male connector 112 is connected to the other end of a tube having a needle provided at one end thereof, the needle being provided to be inserted into a patient. Next, the spike 111 is connected to a medical solution bag in which a medical solution is stored, with the pinch clamp 115 being closed. Next, the pinch clamp 115 is opened so as to fill the flow channel extending from the spike 111 to the needle with the medical solution. This process is generally called "priming". Next, the pinch clamp 115 is closed. Next, the needle is inserted into the vein of a patient. After that, the pinch clamp 115 is opened so as to administer the medical solution to the patient. The flow rate of the medical solution is adjusted by using the roller clip 114. Finally, the pinch clamp 115 is closed so as to stop the administration of the medical solution.

PRIOR ART DOCUMENTS

Patent Documents

Patent Document 1: Japanese Patent No. 3389983
Patent Document 2: JP 2010-75684 A
Patent Document 3: JP 2004-483 A

DISCLOSURE OF INVENTION

Problem to be Solved by the Invention

There are cases where medical solutions contain hazardous medicines designated as powerful medicines such as some anti-cancer agents. It is necessary to avoid situations in which such a medical solution containing a hazardous medicine (hazardous drug) leaks out to the external environment and adheres to the finger or the like of the operator, or the operator inhales the vapor of the medical solution.

With the conventional infusion set 100 described above, during the priming operation of filling the flow channel extending from the spike 111 to the needle that is to be inserted into a patient with a medical solution, the operator may accidentally allow the medical solution to leak from the tip of the needle at the downstream end. If the medical solution contains a hazardous drug, the operator may be exposed to the hazardous drug due to the medical solution leaking out.

The present invention has been made to solve the problems encountered with the above-described conventional infusion set, and it is an object of the present invention to reduce the possibility of a medical solution containing a hazardous drug leaking out to the external environment during a priming operation, and to improve safety.

Means for Solving Problem

An infusion set according to the present invention includes: a first flow channel that is constituted by a pliable tube and includes a spike provided at one end thereof, a second flow channel that is constituted by a pliable tube and includes a lock connector provided at one end thereof, the lock connector including a lock mechanism that is brought into engagement with a female connector; a third flow channel that is constituted by a pliable tube and includes a male connector provided at one end thereof, and a three-way stopcock to which another end of the first flow channel, another end of the second flow channel and another end of the third flow channel are connected. The three-way stopcock includes a handle that can be switched between a first position and a second position, the first position being a position that brings the first flow channel and the third flow channel into communication with each other, and the second position being a position that brings the second flow channel and the third flow channel into communication with each other.

A method for using the above-described infusion set according to the present invention includes: a first priming step of introducing a first liquid through the spike into the first flow channel and the third flow channel in a state in which the handle is set to the first position; a first liquid administering step of administering the first liquid to a patient; a second priming step of introducing a second liquid through the lock connector into the second flow channel by switching the handle to the second position; and a second liquid administering step of administering the second liquid to the patient.

Effects of the Invention

According to the present invention, it is possible to perform the first priming step on the first flow channel and the third flow channel with the handle being set to the first position, and thereafter perform the second priming step on the second flow channel by switching the handle to the second position. As a result of the first priming step being performed using a relatively less hazardous liquid and the second priming step being performed using a medical solution containing a hazardous drug, it is possible to reduce the possibility of the medical solution containing a hazardous drug leaking out to the external environment. Accordingly, the safety of the priming operation can be improved.

BRIEF DESCRIPTION OF DRAWINGS

FIG. 6A is a perspective view of the shield as viewed from above, and FIG. 6B is a perspective view of the same as viewed from below.

FIG. 7A is a perspective view of a female connector to which the lock connector is connected, and FIG. 7B is a cross-sectional view of the same.

DESCRIPTION OF THE INVENTION

Figure 1:
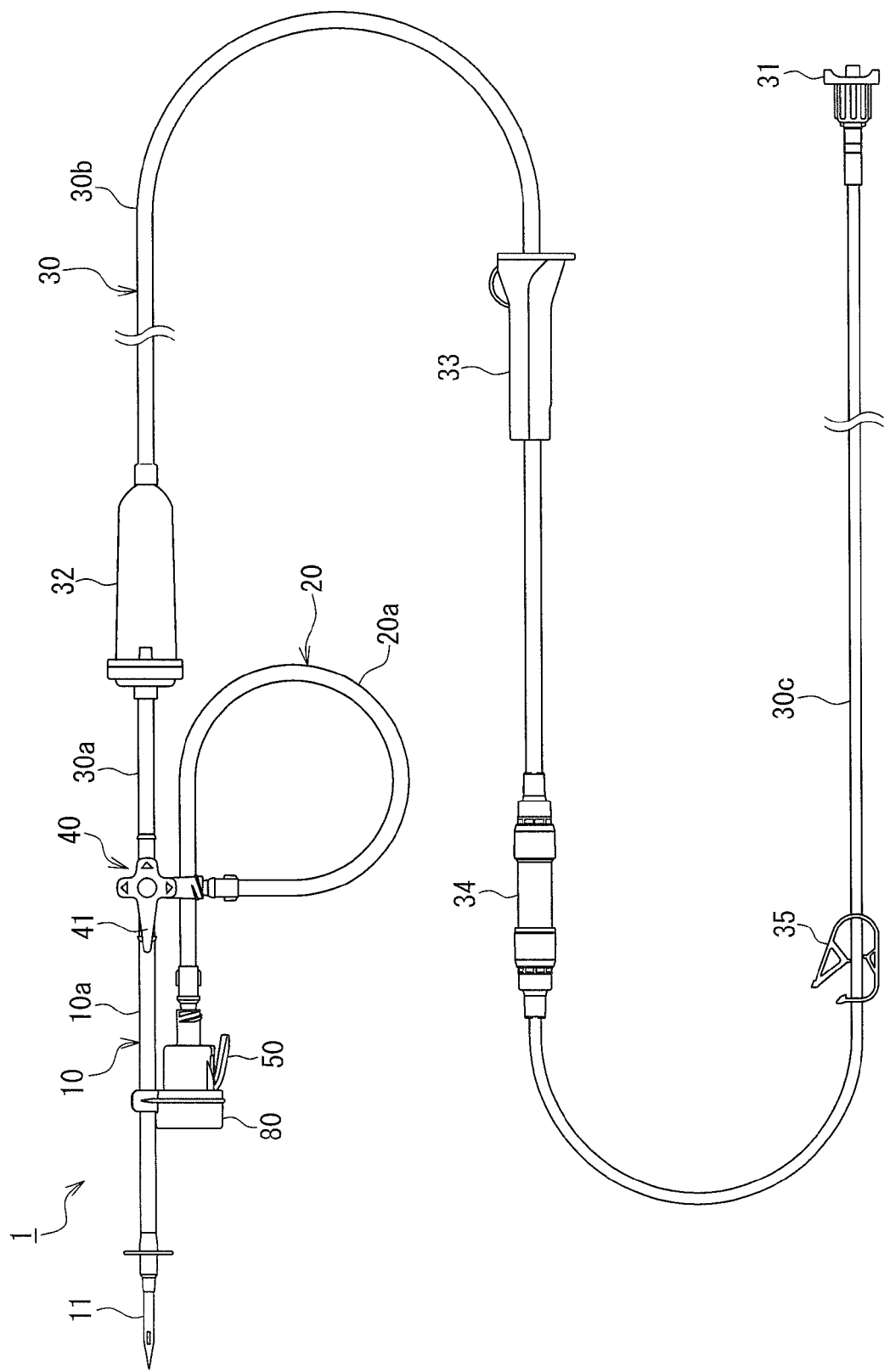
FIG. 1 is a diagram showing an infusion set according to an embodiment of the present invention.

An infusion set according to the present invention includes: a first flow channel that is constituted by a pliable tube and includes a spike provided at one end thereof, a second flow channel that is constituted by a pliable tube and includes a lock connector provided at one end thereof, the lock connector including a lock mechanism that is brought into engagement with a female connector; a third flow channel that is constituted by a pliable tube and includes a male connector provided at one end thereof, and a three-way stopcock to which another end of the first flow channel, another end of the second flow channel and another end of the third flow channel are connected. The three-way stopcock includes a handle that can be switched between a first position and a second position, the first position being a position that brings the first flow channel and the third flow channel into communication with each other, and the second position being a position that brings the second flow channel and the third flow channel into communication with each other.

In the infusion set of the present invention described above, it is preferable that the second flow channel is not in communication with the first flow channel and the third flow channel when the handle is set to the first position, and the first flow channel is not in communication with the second flow channel and the third flow channel when the handle is set to the second position. With this configuration, it is possible to reduce the possibility of a situation occurring in which the flow rate of a medical solution cannot be correctly managed as a result of, for example, unintentionally administering two different medical solutions at the same time to a patient.

In the infusion set of the present invention described above, it is preferable that the third flow channel is provided with a drip chamber and a pinch clamp for opening and closing the third flow channel in this order from a side where the three-way stopcock is provided. With this configuration, in a state in which the third flow channel is closed with the pinch clamp and the handle is set to the second position, a priming operation is performed on the second flow channel by squeezing the drip chamber. It is thereby possible to reduce further the possibility of the medical solution leaking out to the external environment.

It is preferable that the infusion set of the present invention described above further includes a cover that covers a portion of the lock connector, the portion being connected to the female connector, and that can be attached to and detached from the lock connector. With this configuration, before the lock connector is connected to the female connector, the portion of the lock connector that is connected to the female connector can be kept clean. In addition, even if a medical solution still adheres to the lock connector after the lock connector has been disconnected from the female connector, the possibility of the operator accidentally touching the medical solution or inhaling the vapor of the medical solution can be reduced.

It is preferable that the infusion set of the present invention described above further includes a latch structure that allows the lock connector to be latched directly or indirectly to the tube constituting the first flow channel or the tube constituting the third flow channel. With this configuration, when the second flow channel is not in use, by latching the lock connector to the tube constituting the first flow channel or the third flow channel by using the latch structure, the possibility of the tube constituting the second flow channel and the lock connector interfering with the operation can be reduced. The latch structure may be provided on the cover or the lock connector.

In the infusion set of the present invention described above, it is preferable that the lock connector includes a rod-shaped male member including a flow channel through which a liquid flows, and a shield that covers at least a tip of the male member. In this case, it is preferable that the shield includes an outer circumferential wall that has a substantially cylindrical shape and is capable of being elastically compressed and deformed in a lengthwise direction of the male member, and a head portion that is provided at one end of the outer circumferential wall and through which the male member passes when the outer circumferential wall is compressed and deformed. With this configuration, in a state in which the lock connector is not connected to the female connector, the possibility of the medical solution containing a hazardous drug leaking out from the lock connector to the external environment can be reduced.

In this case, it is preferable that a transverse hole in communication with the flow channel has an opening in an outer circumferential surface of the male member in a vicinity of the tip of the male member. It is also preferable that an inner cavity in which the tip of the male member is housed is provided in the head portion. In addition, in a state in which the outer circumferential wall is not compressed or deformed, an inner circumferential surface of the inner cavity comes into close contact with the outer circumferential surface of the male member so as to close the opening of the transverse hole. With this configuration, in a state in which the lock connector is not connected to the female connector, the possibility of the medical solution containing a hazardous drug leaking out from the lock connector to the external environment can be reduced further.

In the infusion set of the present invention described above, it is preferable that a protruding projection portion is provided at a tip position of the head portion through which the male member passes. With this configuration, it is possible to reduce the amount of medical solution remaining on the outer surface of the shield and the outer surface of the female connector after disconnection of the lock connector from the female connector. Accordingly, the possibility of the medical solution containing a hazardous drug leaking out to the external environment can be reduced further.

In the infusion set of the present invention described above, it is preferable that the lock connector includes only one operation arm for performing an operation of disengaging the engagement of the lock mechanism with the female connector. With this configuration, the operation of releasing the locked state established by the lock mechanism can be simplified, and thus the operability is improved.

A method for using the above-described infusion set according to the present invention includes: a first priming step of introducing a first liquid through the spike into the first flow channel and the third flow channel in a state in which the handle is set to the first position; a first liquid administering step of administering the first liquid to a patient; a second priming step of introducing a second liquid through the lock connector into the second flow channel by switching the handle to the second position; and a second liquid administering step of administering the second liquid to the patient.

In the above-described method, it is preferable that the second priming step is performed in a state in which the third flow channel is closed. With this configuration, it is possible to reduce further the possibility of the second liquid leaking out to the external environment during the second priming step.

In the above-described method, it is preferable that the first liquid does not contain a hazardous drug, but the second liquid contains a hazardous drug. With this configuration, it is possible to reduce the possibility of a hazardous drug leaking out to the external environment and the operator being exposed to the hazardous drug. Examples of the hazardous drug include drugs for use in cancer chemotherapy, anti-viral agents, hormone drugs, some biopharmaceutical drugs, and the like. A list of hazardous drugs can be found in appendix A of "NIOSH Alert: Preventing Occupational Exposures to Antineoplastic and Other Hazardous Drugs in Health Care Settings".

Hereinafter, the present invention will be described in detail by illustrating a preferred embodiment. It should be noted, however, that the present invention is not limited to the embodiment given below. For the sake of the convenience of the description, in the diagrams that are referred to in the following description, of the constituent members of the embodiment of the present invention, only primary members that are necessary to describe the present invention are illustrated in a simplified manner. Accordingly, the present invention may include arbitrary constituent members that are not illustrated in the diagrams mentioned below. Also, the dimensions of the members shown in the diagrams mentioned below are not true to the actual dimensions of the constituent elements and the dimension ratio of the members.

<Overall Configuration of Infusion Set 1>

FIG. 1 is a diagram showing an infusion set 1 according to an embodiment of the present invention.

The infusion set 1 includes a first flow channel 10, a second flow channel 20, a third flow channel 30, and a three-way stopcock 40.

The first flow channel 10 is constituted by a pliable tube 10a. A spike 11 is provided at one end of the first flow channel 10, and the other end is connected to the three-way stopcock 40. The spike 11 is inserted into a port of a first medical solution bag (not shown) in which a premedication, such as an antiemetic, that is administered before administration of an anti-cancer agent is stored. The configuration of the spike 11 is arbitrary. For example, it is possible to use a resin needle having a sharp tip that can be inserted into a rubber stopper provided in the port of the first medical solution bag.

The second flow channel 20 is constituted by a pliable tube 20a. A lock connector 50 is provided at one end of the second flow channel 20, and the other end is connected to the three-way stopcock 40. The lock connector 50 is connected to a port (female connector) of a second medical solution bag (not shown) in which an anti-cancer agent is stored. A cover 80 is attached to a side of the lock connector 50 that is connected to the female connector. The cover 80 is latched to the tube 10a. The configurations of the lock connector 50 and the cover 80 will be described later.

The third flow channel 30 is constituted by pliable tubes 30a, 30b and 30c. One end of the third flow channel 30 is connected to the three-way stopcock 40, and a male connector 31 is provided at the other end. The third flow channel 30 is provided with a drip chamber 32, a roller clip 33, a filter 34, and a pinch clamp 35.

The male connector 31 is connected to a female connector provided at an upstream end of a tube having a needle at a downstream end thereof, the needle being provided to be inserted into the vein of a patient. The configuration of the male connector 31 is arbitrary. The male connector 31 may include, for example, a male luer that conforms to ISO 594-1. In order to prevent unintentional disconnection of the male connector 31 and the female connector that have been connected to each other, it is preferable that the male connector 31 and the female connector are provided with engagement structures that engage with each other.

The drip chamber 32 is connected between the tube 30a and the tube 30b. The drip chamber 32 allows the flow rate of the medical solution flowing through the third flow channel 30 to be checked visually. The drip chamber 32 is also useful for performing a so-called priming operation of introducing a medical solution into the infusion set 1 by being squeezed with the fingers.

The roller clip 33 is provided on the tube 30b. The roller clip 33 allows the flow rate of the medical solution flowing through the third flow channel 30 to be set as desired through adjustment of the cross sectional area of the medical solution flow channel of the tube 30b.

The filter 34 is connected between the tube 30b and the tube 30c. The filter 34 catches fine debris generated from the rubber stopper when the spike 11 pierces the rubber stopper, and solids in the medical solution such as undissolved medicine in the medical solution.

The pinch clamp 35 is provided on the tube 30c. The pinch clamp 35 switches the flow of the medical solution flowing through the third flow channel 30 between on and off by opening and closing the medical solution flow channel of the tube 30c.

There is no particular limitation on the configurations of the drip chamber 32, the roller clip 33, the filter 34 and the pinch clamp 35, and they may have arbitrary configurations.

The three-way stopcock 40 includes three connection ports. A first connection port is connected to a downstream end of the tube 10a constituting the first flow channel 10. A second connection port is connected to a downstream end of the tube 20a constituting the second flow channel 20. A third connection port is connected to an upstream end of the tube 30a constituting the third flow channel 30. The three-way stopcock 40 includes a handle 41 that is pivotable about a pivot shaft between a "first position" and a "second position". FIG. 1 shows the handle 41 set at the first position. When the handle 41 is set to the first position, the three-way stopcock 40 brings the first flow channel 10 and the third flow channel 30 into communication with each other. At this time, it is preferable that the second flow channel 20 is not in communication with the first flow channel 10 and the third flow channel 30. When the handle 41 is set to the second position, the three-way stopcock 40 brings the second flow channel 20 and the third flow channel 30 into communication with each other. At this time, it is preferable that the first flow channel 10 is not in communication with the second flow channel 20 and the third flow channel 30. The three-way stopcock 40 may have an arbitrary configuration as long as it is possible to switch the flow channels as described above. Among known three-way stopcocks, there is a three-way stopcock whose handle can be pivoted to a "third position" that brings the first flow channel 10, the second flow channel 20 and the third flow channel 30 into communication with each other, but such a three-way stopcock causes a possibility of the operator making an erroneous operation of simultaneously administering both the medical solution contained in the first medical solution bag and the medical solution contained in the second medical solution bag to a patient. Accordingly, it is preferable to use, as the three-way stopcock 40 that constitute the infusion set of the present invention, a three-way stopcock whose handle cannot be pivoted to the third position.

The tubes (the tubes 10a, 20a, 30a, 30b and 30c) constituting the flow channels 10, 20 and 30 of the infusion set 1 preferably have the same outer and inner diameters. There is no particular limitation on the material of the tubes, and it is possible to use a pliable material, such as soft vinyl chloride, polybutadiene, or polyethylene.

<Lock Connector 50>

Figure 2:
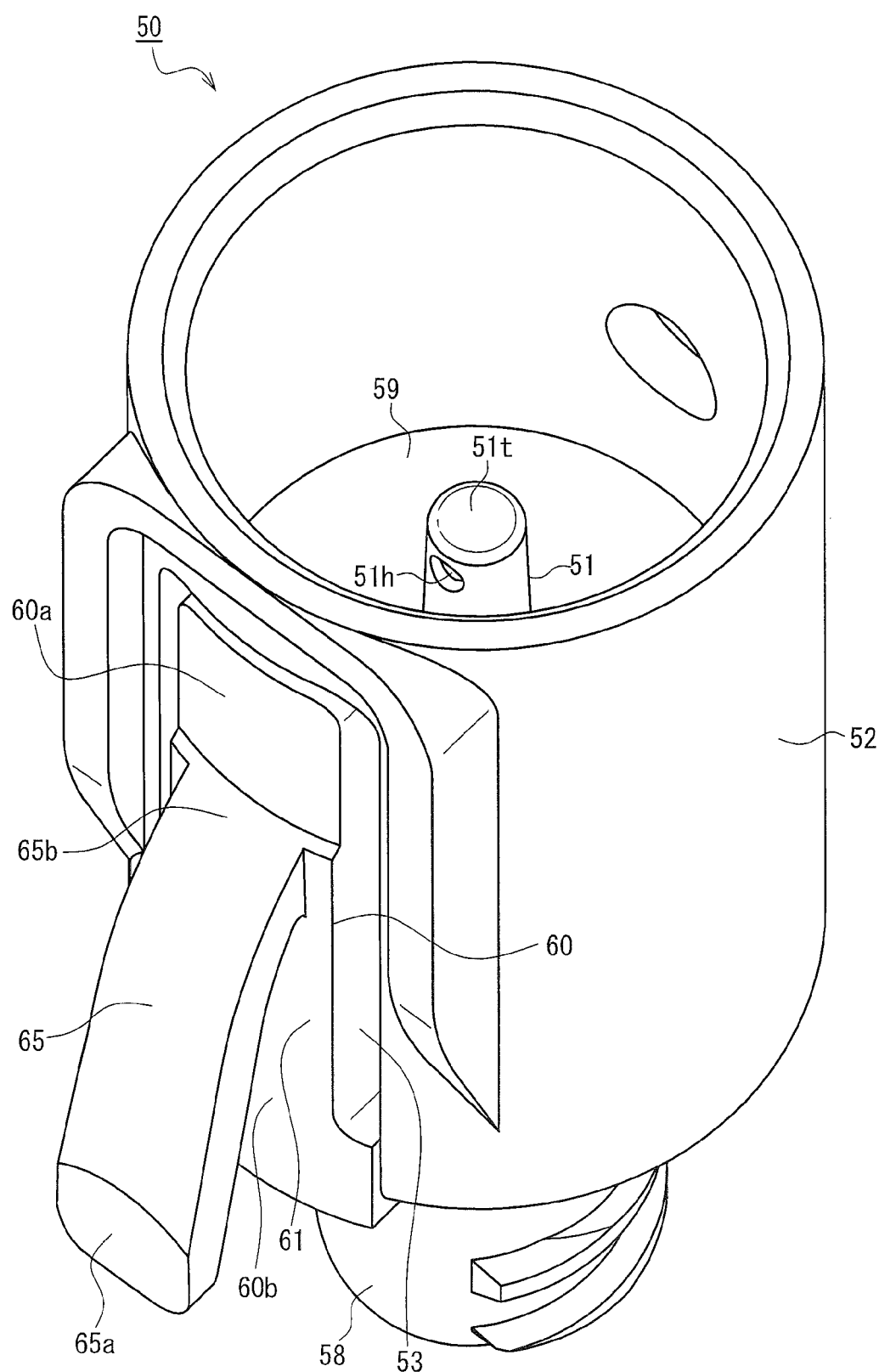
FIG. 2 is a perspective view of a lock connector included in the infusion set according to an embodiment of the present invention.
Figure 3:
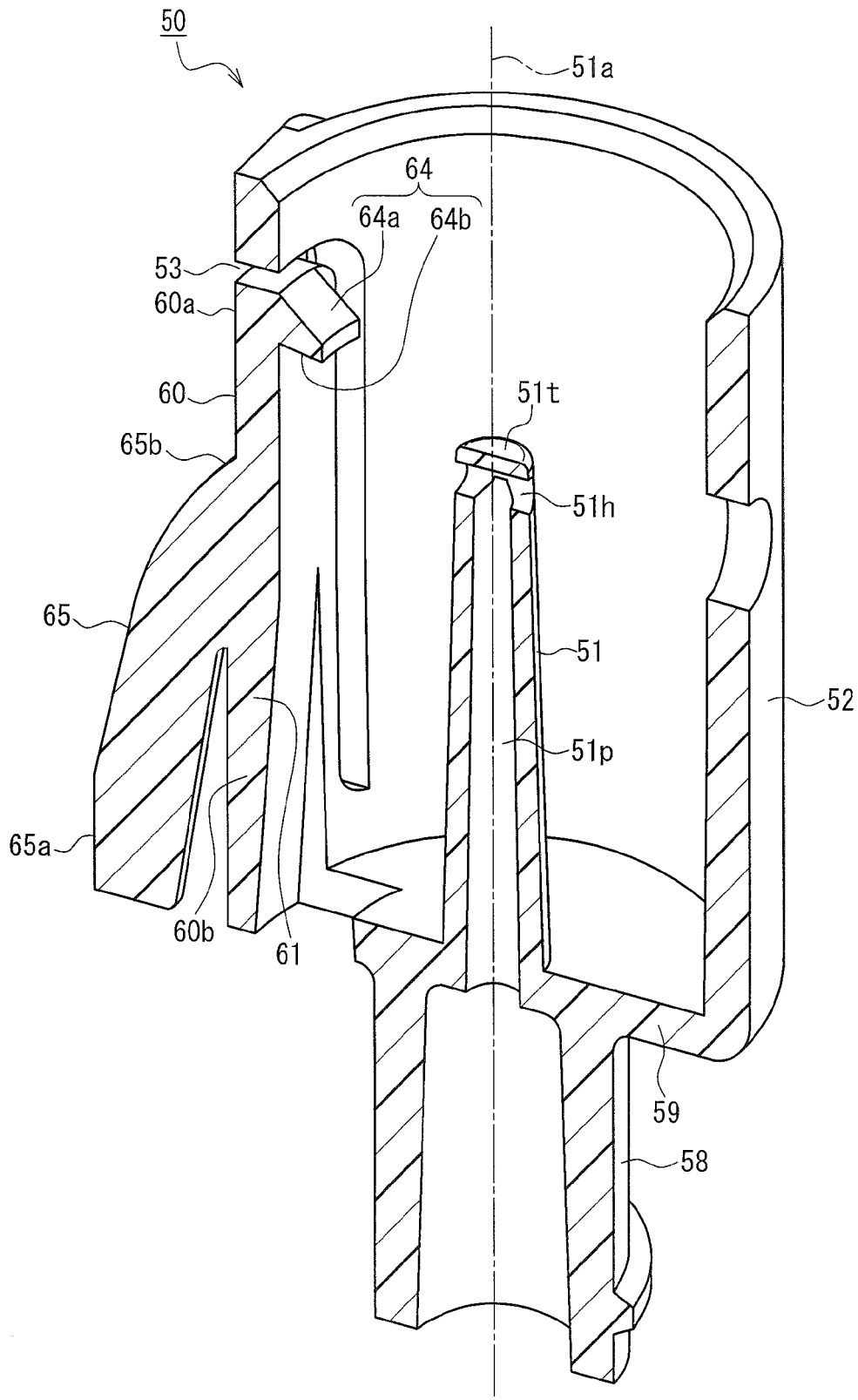
FIG. 3 is a perspective cross-sectional view of the lock connector shown in FIG. 2.

FIG. 2 is a perspective view of the lock connector 50 included in the infusion set according to an embodiment of the present invention. FIG. 3 is a perspective cross-sectional view of the lock connector 50. In FIGS. 2 and 3, in order to simplify the illustration, a shield 70 (see FIG. 5), which will be described later, is not shown.

The lock connector 50 includes a rod-shaped male luer 51 as a male member. In FIG. 3, reference numeral 51a indicates the central axis of the male luer 51. For the sake of the convenience of the description given below, a lengthwise direction of the male luer 51 (a direction parallel to the central axis 51a) will be referred to the "up-down direction". Likewise, a direction of a straight line perpendicular to the central axis 51a will be referred to as the "radial direction", and a direction of rotation about the central axis 51a will be referred to as the "circumferential direction".

As shown in FIG. 3, the male luer 51 is a rod-shaped member protruding from a disc-shaped base 59. In the present embodiment, the male luer 51 has an outer circumferential surface (or in other words, side surface) that is a tapered surface whose outer diameter decreases gradually as the distance from the base 59 increases. However, the shape of the outer circumferential surface of the male luer 51 is not limited thereto, and can be selected as desired. For example, the outer circumferential surface may be a cylindrical surface whose outer diameter is constant in the up-down direction.

A flow channel 51p is formed in the male luer 51 so as to extend along the lengthwise direction of the male luer 51. The flow channel 51p does not have an opening at a tip surface 51t of the male luer 51. Instead, in the vicinity of the tip of the male luer 51, a transverse hole 51h that is in communication with the flow channel 51p is formed. The transverse hole 51h passes through the male luer 51 in the radial direction, and has two openings in the outer circumferential surface of the male luer 51. The transverse hole 51h may have only one opening in the outer circumferential surface of the male luer 51 without passing through the male luer 51.

On a side of the base 59 opposite to the side where the male luer 51 is provided, a tubular member 58 having a flow channel is formed in communication with the flow channel 51p. The tubular member 58 has an inner circumferential surface that is a tapered surface whose inner diameter increases gradually as the distance from the base 59 increases. The tubular member 58 has an externally threaded outer circumferential surface. The tubular member 58 conforms to ISO594-2. Although not shown in the diagram, a male connector conforming to ISO594-2 is provided at the upstream end of the tube 20a (see FIG. 1) constituting the second flow channel 20. As a result of the male connector being connected to the tubular member 58, the second flow channel 20 is brought into communication with the flow channel 51p formed in the male luer 51. However, the connection method for connecting the lock connector 50 and the tube 20a is not limited thereto. The lock connector 50 and the tube 20a may be connected directly to each other by, for example, inserting the tubular member 58 having a cylindrical outer circumferential surface into the upstream end of the tube 20a.

A hood 52 is provided upright on the base 59 on the same side as the male luer 51 so as to surround the male luer 51. The hood 52 has a hollow cylindrical shape that is concentric with the male luer 51, and a height (up-down direction dimension) that is higher than the height of the male luer 51. The hood 52 has an inner circumferential surface (a surface facing the male luer 51) that is a cylindrical surface.

A lock lever 60 with a cantilevered support structure is provided so as to face the male luer 51. The lock lever 60 has a thin plate shape (strip shape) whose lengthwise direction is substantially parallel to the central axis 51a of the male luer 51. One of the lengthwise ends of the lock lever 60 is a free end 60a, which is disposed on the male luer 51 tip side of the lock lever. The other lengthwise end of the lock lever 60 is a fixed end 60b, which is disposed on the male luer 51 proximal end side (or in other words, the base 59 side) of the lock lever. The lock lever 60 is capable of being elastically bent and deformed within a plane including the central axis 51a of the male luer 51.

The lock lever 60 with a cantilevered support structure is formed in the hood 52 by forming a substantially U-shaped slit 53 passing through the hood 52. In other words, the lock lever 60 is surrounded by the slit 53.

A hook 64 protruding toward the male luer 51 is formed on a surface of the free end 60a of the lock lever 60, the surface facing the male luer 51. The hook 64 includes an inclined surface 64a and an engagement surface 64b. The inclined surface 64a is inclined so as to be further away from the male luer 51 as the distance from the base 59 increases. The engagement surface 64b is a flat surface that is disposed closer to the base 59 side than the inclined surface 64a is, and is substantially parallel to a horizontal direction (a direction parallel to the plane perpendicular to the central axis 51a). A top portion (a portion located at a position closest to the male luer 51) of the hook 64 protrudes toward the male luer 51 more than the inner circumferential surface of the hood 52 does.

An operation arm 65 protrudes externally (toward the side opposite to the male luer 51) from a surface of the lock lever 60 that is opposite to the male luer 51. A portion of the operation arm 65 that is connected to the lock lever 60 will be referred to as a proximal end 65b. It is preferable that the proximal end 65b is positioned closer to the free end 60a side than the fixed end 60b of the lock lever 60 (or in other words, the proximal end 65b is not present on the fixed end 60b). The operation arm 65 curves from the proximal end 65b toward the fixed end 60b so as to be spaced apart from the lock lever 60. In the direction parallel to the central axis 51a, the operation arm 65 extends to a position below (toward the tubular member 58) the fixed end 60b of the lock lever 60 (in the present embodiment, to a position substantially the same as the base 59). The operation arm 65 includes an operating portion 65a provided at a tip thereof. The operation arm 65 has a mechanical strength enough to be deemed as a substantially rigid body.

Figure 4:
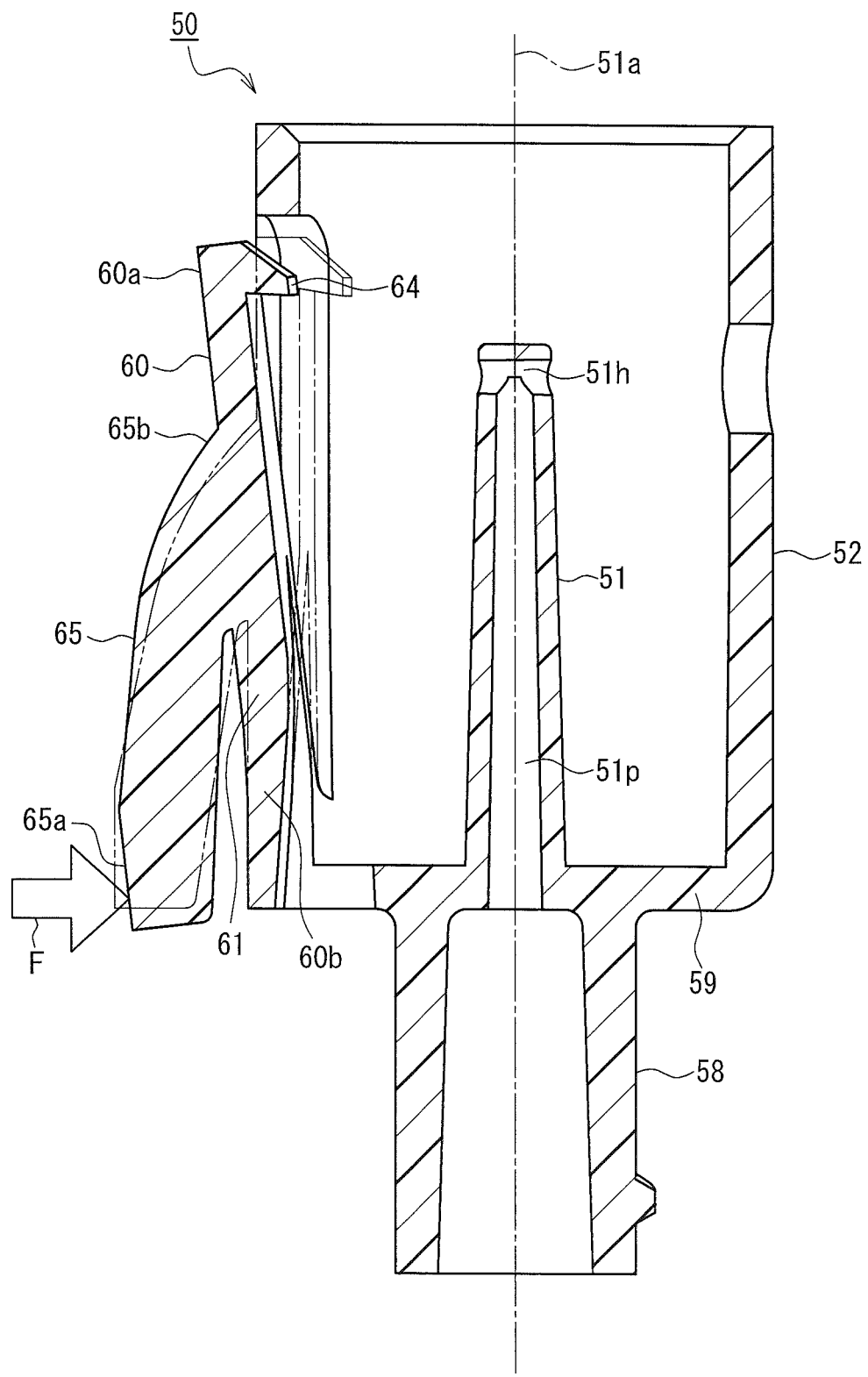
FIG. 4 is a cross-sectional view of the lock connector shown in FIG. 2, showing a lock lever that has been elastically deformed.

If a pressing force F directed toward the male luer 51 (or in other words, the hood 52) is applied to the operating portion 65a by a finger pressing against the operating portion 65a, as shown in FIG. 4, a portion (elastic portion 61) between the fixed end 60b of the lock lever 60 and the proximal end 65b of the operation arm 65 is elastically bent and deformed, whereby the hook 64 is displaced in a direction away from the male luer 51 along a substantially radial direction.

The hood 52 and the lock lever 60 equipped with the operation arm 65 described above constitute a lock mechanism of the lock connector 50.

The lock connector 50 is preferably made of a hard material. To be specific, the lock connector 50 can be made by a method such as integral molding using a resin material such as polyacetal, polycarbonate, polystyrene, polyamide, polypropylene, or hard poly(vinyl chloride).

Figure 5:
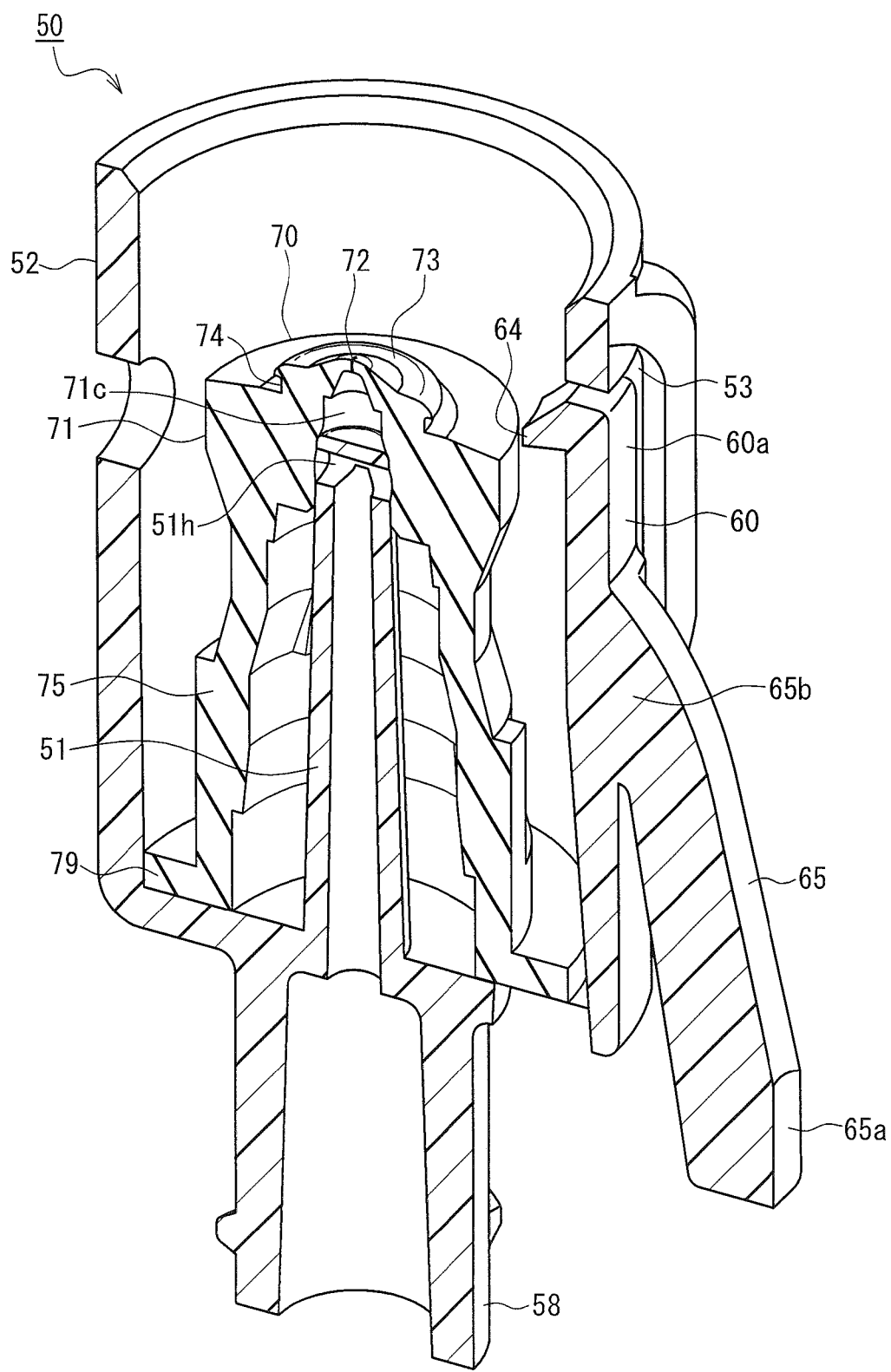
FIG. 5 is a perspective cross-sectional view of the lock connector shown in FIG. 2 in which a shield is attached to a male luer.

In the present embodiment, as shown in FIG. 5, the male luer 51 is covered with a shield 70. FIG. 6A is a perspective view of the shield 70 as viewed from above, and FIG. 6B is a perspective view of the shield 70 as viewed from below. The shield 70 includes an outer circumferential wall 75 that is substantially cylindrical in shape, a head portion 71 provided at one end of the outer circumferential wall 75, and an annular bottom portion 79 provided at the other end of the outer circumferential wall 75. The shield 70 can be integrally made by using a flexible (pliable) material (for example, silicone rubber or isoprene rubber).

Upon application of a compressive force in the up-down direction to the shield 70, the outer circumferential wall 75 is elastically compressed and deformed such that its dimension in the up-down direction is shortened (see FIG. 10 described later). As shown in FIG. 5, the outer circumferential wall 75 is internally provided with a space into which the male luer 51 can be inserted. Furthermore, the inner circumferential surface of the outer circumferential wall 75 and the male luer 51 preferably are spaced apart from each other so as to, when the outer circumferential wall 75 is compressed and deformed in the up-down direction, not limit the compression and deformation of the outer circumferential wall 75 in the up-down direction as a result of the inner circumferential surface of the outer circumferential wall 75 colliding with the male luer 51.

As shown in FIG. 5, the head portion 71 includes an inner cavity 71c that is in communication with the internal space of the outer circumferential wall 75. A tip portion of the male luer 51 including an opening forming the transverse hole 51h is inserted into the inner cavity 71c. The shape of the inner circumferential surface of the inner cavity 71c is arbitrary, and it may be a shape extending along the outer circumferential surface of the male luer 51. It is preferable that the inner diameter of the inner cavity 71c is set to be slightly smaller than the outer diameter of the male luer 51 such that the inner circumferential surface of the inner cavity 71c is brought into close contact with the outer circumferential surface of the male luer 51. The opening forming the transverse hole 51h is sealed in a liquid tight manner by the inner circumferential surface of the inner cavity 71c.

A slit 72 passing through the head portion 71 in the up-down direction is formed at the deepest portion of the inner cavity 71c. As shown in FIG. 6A, the slit 72 is a linear cut in the shape of a minus sign ("–") as viewed from above. In a normal state in which the male luer 51 is not passing through the slit 72, it is preferable that the facing edges forming the slit 72 are in contact with each other and form a liquid-tight seal therebetween.

On an upper surface of the head portion 71, a projection portion 73 having a substantially mushroom shape protruding upwardly from the upper surface is disposed. The projection portion 73 preferably has an upper surface having a convexly curved surface that is smoothly rounded in a dome shape such as a substantially conical surface, a substantially frustoconical surface, or a spherical surface. The slit 72 passes through the topmost portion (center) of the projection portion 73. The projection portion 73 includes, below its upper surface, a neck portion (narrowed portion) 74 having a relatively reduced outer diameter.

The bottom portion 79 is provided to fix the shield 70 to the base 59 of the lock connector 50. There is no particular limitation on the method for fixing the bottom portion 79 to the base 59, and it is possible to use any method such as bonding, welding, engaging or fitting. The shape of the bottom portion 79 can be set as desired according to the fixing method.

Figure 8:
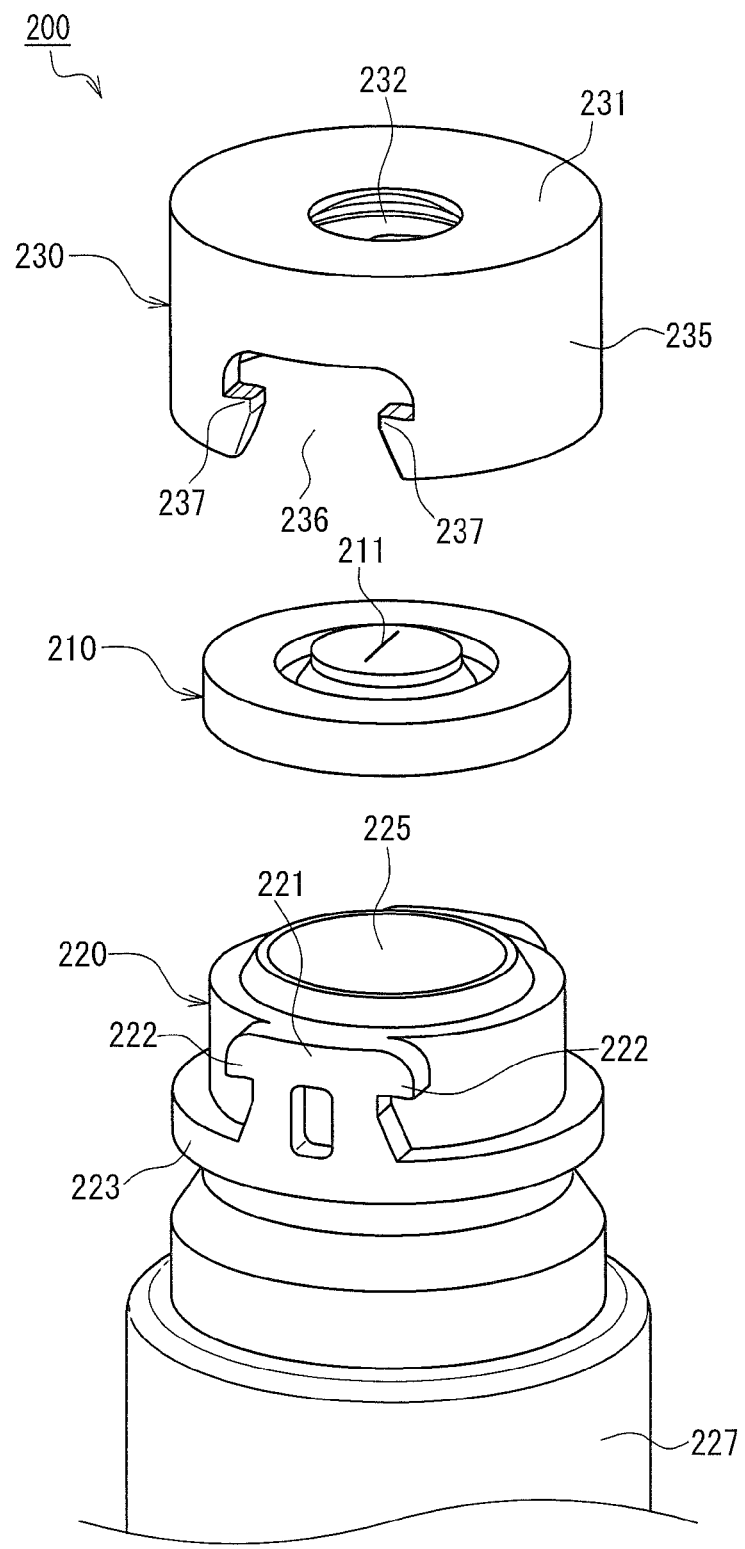
FIG. 8 is an exploded perspective view of the female connector to which the lock connector is connected.

FIG. 7A is a perspective view of a female connector 200 to which the lock connector 50 is connected, and FIG. 7B is a cross-sectional view of the female connector 200. In FIG. 7B, reference numeral 200a indicates the central axis of the female connector 200. For the sake of the convenience of the description given below, a direction parallel to the central axis 200a will be referred to as the "up-down direction" of the female connector 200. A direction of a straight line perpendicular to the central axis 200a will be referred to as the "radial direction", and a direction of rotation about the central axis 200a will be referred to as the "circumferential direction". FIG. 8 is an exploded perspective view of the female connector 200.

The female connector 200 includes a disc-shaped partition member (hereinafter referred to as a "septum") 210, and a base platform 220 and a cap 230 that sandwich the septum 210 in the up-down direction so as to fix the septum 210.

The septum 210 is made of an elastic material such as rubber, and includes, at a central portion thereof, a linear slit (cut) 211 passing through the septum 210 in the up-down direction.

The base platform 220 has a substantially cylindrical shape as a whole. The base platform 220 has an outer circumferential surface which is a cylindrical surface. On the outer circumferential surface, a pair of engagement protrusions 221 and an annular protrusion 223 that is continuous in the circumferential direction are formed so as to protrude outwardly in the radial direction. Each engagement protrusion 221 includes a pair of engagement tabs 222 protruding in the circumferential direction, and has a substantially T shape as a whole. The annular protrusion 223 is provided below the engagement protrusions 221 (on the side opposite to the septum 210). Top portions (portions farthest from the central axis 200a) of the engagement protrusions 221 and the annular protrusion 223 constitute a common cylindrical surface concentric with the central axis 200a.

Although not shown, a portion (proximal end) 227 below the annular protrusion 223 of the base platform 220 is fixed to a second medical solution bag in which an anti-cancer agent is stored. Alternatively, the second medical solution bag and the proximal end 227 may be connected via a pliable tube or the like.

The cap 230 includes a disk-shaped top plate 231 and a cylindrical peripheral wall 235 extending downwardly from an outer circumferential end edge of the top plate 231. The top plate 231 has a circular opening (through hole) 232 formed in the center thereof. In the peripheral wall 235, a pair of cutouts 236 upwardly cut out from the lower end of the peripheral wall 235 are formed. Each cutout 236 has a circumferential dimension that is locally narrowed by a pair of engagement tabs 237.

The septum 210 is placed on the upper end of the base platform 220, and the cap 230 is capped from above the septum 210. The engagement protrusions 221 formed on the base platform 220 are fitted into the cutouts 236 formed in the cap 230, as a result of which the engagement tabs 222 and the engagement tabs 237 are engaged. In this way, the cap 230 is fixed to the base platform 220 (see FIG. 7A). The septum 210 is sandwiched in the thickness direction (or in other words, in the up-down direction) by the upper end of the base platform 220 and the top plate 231 of the cap 230. The slit 211 of the septum 210 is exposed within the opening 232 formed in the top plate 231. The annular protrusion 223 formed on the base platform 220 is positioned below the peripheral wall 235 of the cap 230. The top portions of the engagement protrusions 221 and the annular protrusion 223 constitute substantially the same cylindrical surface as the outer circumferential surface of the peripheral wall 235.

There is no particular limitation on the material of the septum 210, and it is preferable to use a soft material. For example, isoprene rubber, silicone rubber, butyl rubber, thermoplastic elastomer or the like can be used. Likewise, there is no particular limitation on the materials of the base platform 220 and the cap 230, and it is preferable to use hard materials. For example, polycarbonate, polypropylene, polyacetal, polyamide, hard poly(vinyl chloride), polyethylene and the like can be used.

A method for connecting and disconnecting the lock connector 50 to and from the female connector 200 will be described.

Figure 9:
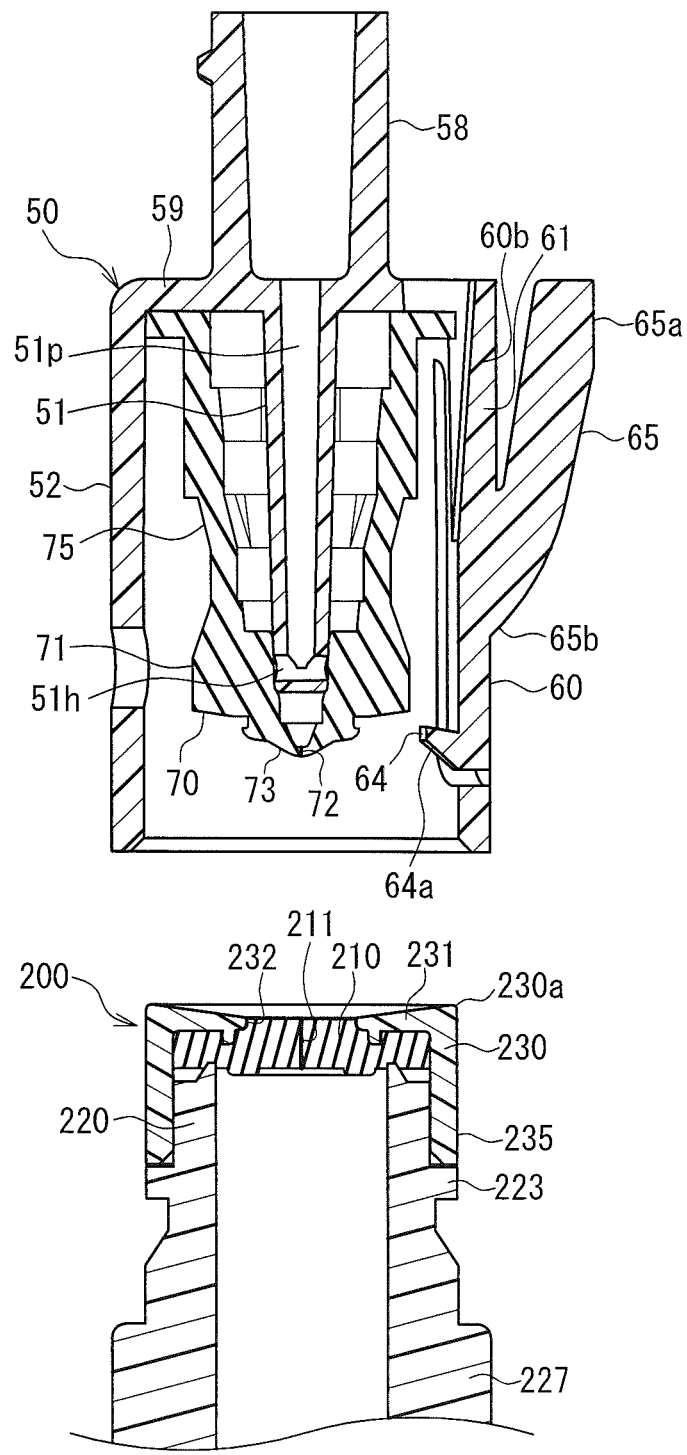
FIG. 9 is a cross-sectional view of the lock connector before it is connected to the female connector.

As shown in FIG. 9, the lock connector 50 and the female connector 200 are arranged so as to face each other. Then, the cap 230 of the female connector 200 is inserted into the hood 52 of the lock connector 50, and the female connector 200 is pressed against the lock connector 50. The projection portion 73 protruding from the head portion 71 of the shield 70 collides with the septum 210 of the female connector 200. After that, the male luer 51 is admitted into the slit 72 formed in the head portion 71, and then into the slit 211 of the septum 210. Through this process, the shield 70 is elastically compressed and deformed in the lengthwise direction of the male luer 51. In parallel with this process, the inclined surface 64a of the hook 64 of the lock lever 60 comes into abutment with an outer end edge 230a of the top plate 231 of the cap 230. The outer end edge 230a slides over the inclined surface 64a, thereby causing the elastic portion 61 to be elastically bent and deformed and the lock lever 60 to be displaced such that the hook 64 is moved away from the male luer 51. The hook 64 slides over the peripheral wall 235 of the cap 230 and the annular protrusion 223 in this order as the female connector 200 is admitted into the hood 52. Then, when the hook 64 has passed through the annular protrusion 223, the elastic portion 61 is elastically restored, and the hook 64 and the annular protrusion 223 are thereby engaged (locked state).

Figure 10:
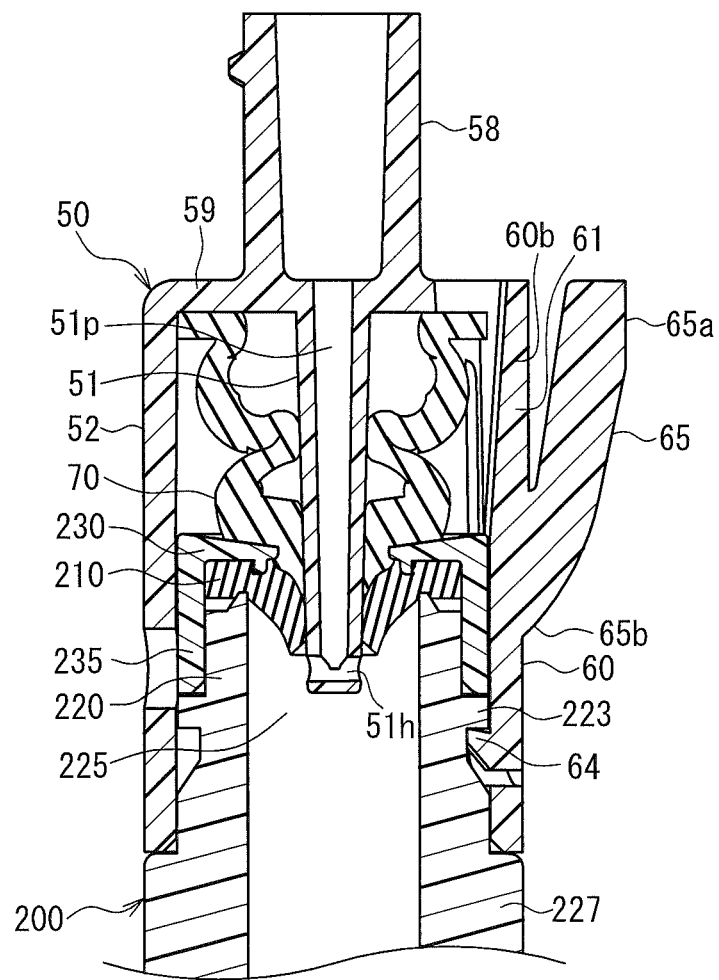
FIG. 10 is a cross-sectional view of the lock connector after being connected to the female connector.

FIG. 10 is a cross-sectional view of the lock connector 50 that has been connected to the female connector 200 and is in the locked state.

The lock lever 60 is at substantially the same position as the initial state (see FIG. 9), and the hook 64 (in particular, the engagement surface 64b (see FIG. 3)) is in engagement with the annular protrusion 223 of the female connector 200. The male luer 51 is passing through the slit 72 formed in the head portion 71 of the shield 70 (see FIG. 9), and the slit 211 of the septum 210 (see FIG. 9). The shield 70, in particular, the outer circumferential wall 75 (see FIG. 9) is elastically compressed and deformed to a significant degree under compressive force in the up-down direction. The septum 210 is passed through by the male luer 51 and thus elastically deformed to a significant degree. The opening forming the transverse hole 51h of the male luer 51 is exposed within an inner cavity 225 formed in the base platform 220. In this state, a medical solution can be allowed to flow between the lock connector 50 and the female connector 200 via the flow channel 51p, the transverse hole 51h and the inner cavity 225.

The lock connector 50 and the female connector 200 can be disconnected by pressing the operating portion 65a of the lock lever 60 with a finger and displacing the lock lever 60 such that the hook 64 is moved away from the male luer 51 (see FIG. 4). By doing so, the engagement between the hook 64 and the annular protrusion 223 is disengaged. In parallel with this, by pulling the lock connector 50 and the female connector 200 apart from each other, the lock connector 50 and the female connector 200 can be disconnected.

As the male luer 51 is pulled out from the septum 210, the outer circumferential wall 75 of the shield 70 is elastically restored and extended. The male luer 51 is moved relative to the septum 210 and the head portion 71, with the projection portion 73 (see FIG. 9) of the head portion 71 of the shield 70 remaining in close contact with the septum 210. Through this process, the end edge of the slit 211 of the septum 210 and the end edge of the slit 72 of the head portion 71 slide over the outer circumferential surface of the male luer 51, and thereby the medical solution adhering to the outer circumferential surface of the male luer 51 is removed.

After the male luer 51 has been pulled out of the slit 211 of the septum 210, the septum 210 is immediately elastically restored back to its original shape, and the slit 211 is closed to form a liquid-tight seal. After that, when the male luer 51 has been pulled out of the slit 72 of the head portion 71 of the shield 70, the slit 72 is immediately elastically restored and closed to form a liquid-tight seal. The transverse hole 51h of the male luer 51 and its vicinity portion is housed within the inner cavity 71c of the head portion 71. The inner circumferential surface of the inner cavity 71c comes into close contact with the outer circumferential surface of the male luer 51 so as to close the opening forming the transverse hole 51h. After that, the projection portion 73 of the head portion 71 is moved apart from the septum 210, and returns to its initial state shown in FIG. 9.

<Cover 80>

Figure 11A:
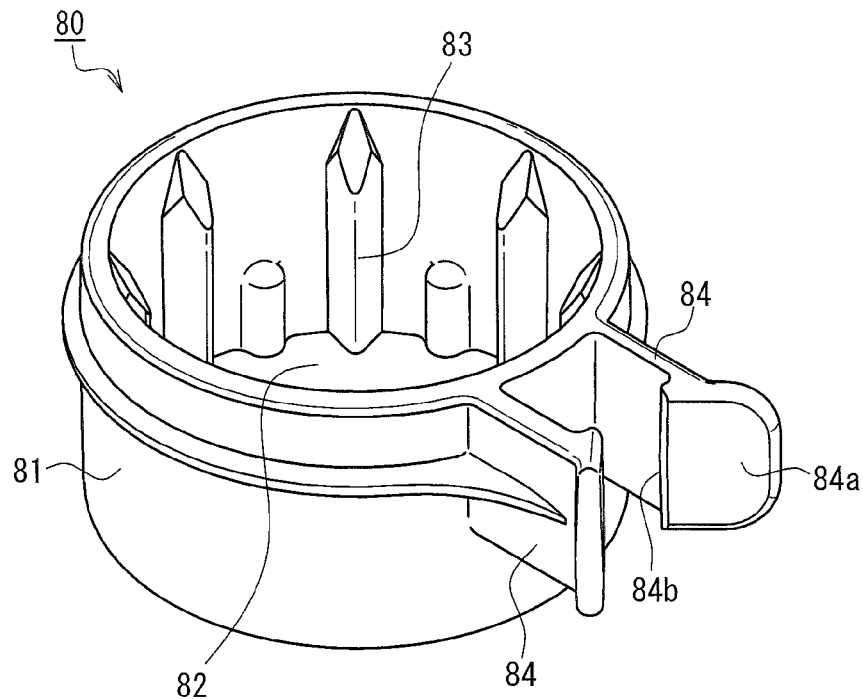
FIG. 11A is a perspective view of a cover included in the infusion set according to an embodiment of the present invention.
Figure 11B:
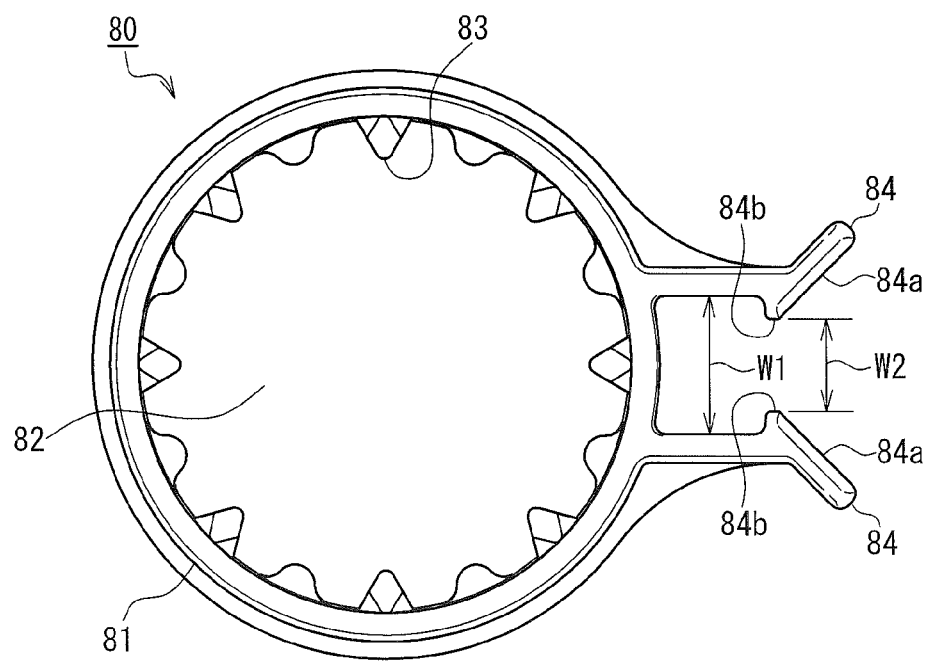
FIG. 11B is a top view of the cover.

FIG. 11A is a perspective view of the cover 80, and FIG. 11B is a top view of the cover 80 as viewed from the side to which the lock connector 50 is attached. The cover 80 includes a cylindrical outer wall 81 and a bottom plate 82 closing one of the openings of the outer wall 81. A plurality of ribs 83 extending in a direction vertical to the bottom plate 82 protrude from an inner circumferential surface of the outer wall 81. A pair of arms 84 protrude from an outer circumferential surface of the outer wall 81. The pair of arms 84 are spaced apart from each other and are substantially parallel to each other. The pair of arms 84 have, at their tips, inclined surfaces 84a inclined such that the spacing between the pair of arms 84 increases as their distance from the outer wall 81 increases. The spacing between the pair of arms 84 is smallest at latch portions 84b, which are end portions of the inclined surfaces 84a closest to the outer wall 81. Where the outer diameter of the tubes (in particular, a tube constituting the first flow channel 10 and a tube constituting the third flow channel 30) included in the infusion set 1 is represented by D, a spacing W1 (see FIG. 11B) between the pair of arms 84 in a region located at a position closer to the outer wall 81 side than the latch portions 84b is preferably the same as or larger than the outer diameter D, and a spacing W2 (see FIG. 11B) between the pair of arms 84 at the latch portions 84b is preferably smaller than the outer diameter D.

Figure 12:
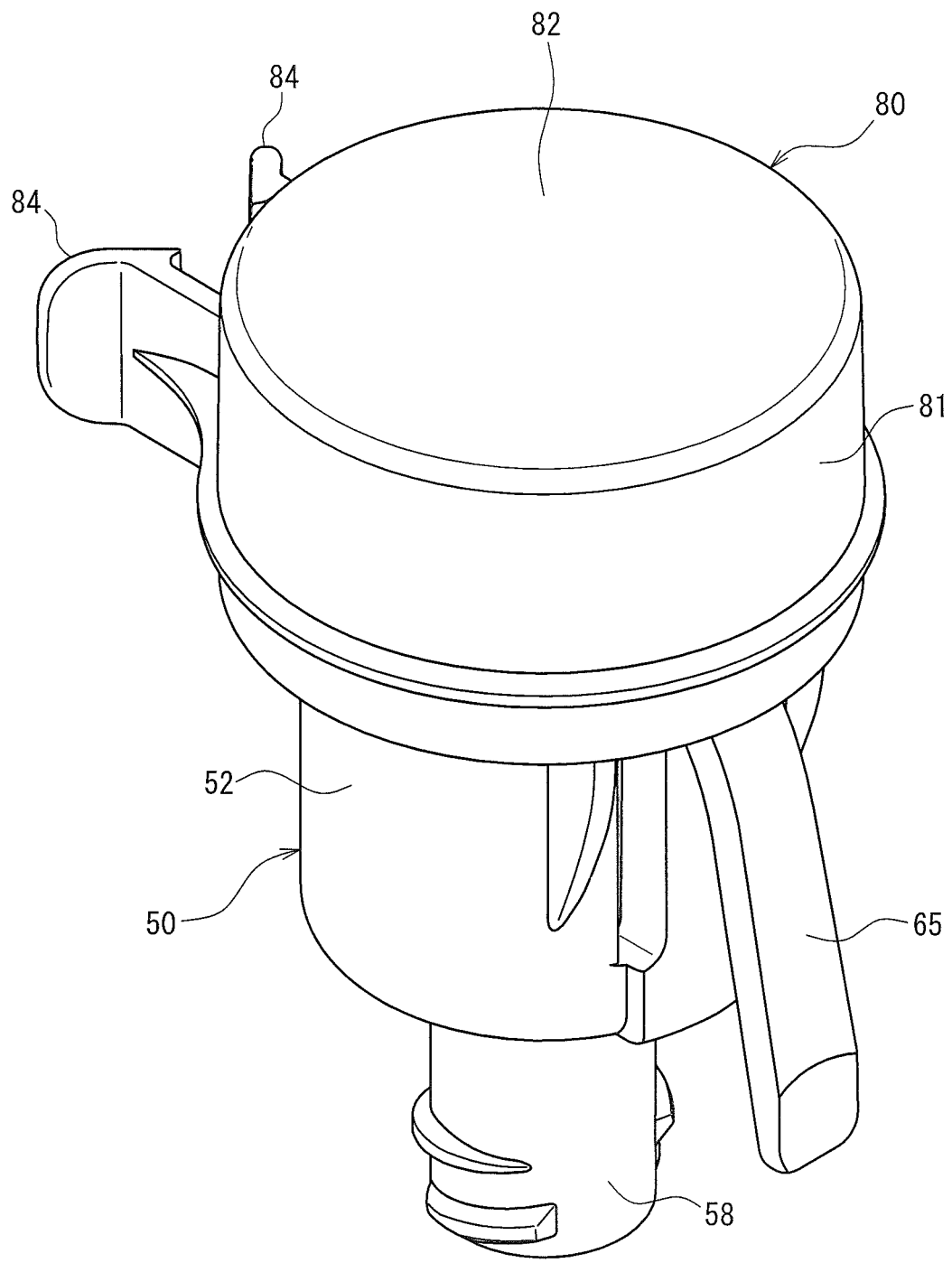
FIG. 12 is a perspective view of the lock connector to which the cover has been attached

As shown in FIG. 12, the cover 80 is attached to the hood 52 of the lock connector 50 so as to close the upper opening of the hood 52. Because the ribs 83 come into close contact with the outer circumferential surface of the hood 52, the cover 80 and the lock connector 50 will not be disconnected by vibrations, a slight external force or the like.

As shown in FIG. 1, the cover 80 can be latched to the tube 10a by fitting the tube 10a in between the pair of arms 84 of the cover 80. The lock connector 50 is latched to the tube 10a via the cover 80. The cover 80 and the lock connector 50 may be latched to any tube of the infusion set 1 other than the tube 10a (for example, a tube constituting the third flow channel 30).

The cover 80 is preferably made of a hard material. To be specific, the cover 80 can be made by a method such as integral molding using a resin material such as polyacetal, polycarbonate, polystyrene, polyamide, polypropylene, or hard poly(vinyl chloride).

<Usage of Infusion Set 1>

A method for administering an anti-cancer agent with the use of the infusion set 1 configured as above will be described.

As shown in FIG. 1, in the initial state of the infusion set 1, the cover 80 is attached to the lock connector 50, and the cover 80 is latched to the tube 10a. The handle 41 of the three-way stopcock 40 is set to the first position that brings the first flow channel 10 and the third flow channel 30 into communication with each other. The roller clip 33 and the pinch clamp 35 are open.

First, the male connector 31 is connected to an upstream end of a tube having a needle provided at a downstream end thereof, the needle being provided to be inserted into the vein of a patient. Next, the spike 11 is connected to a port of a first medical solution bag in which a premedication (first liquid) is stored, and the flow channel extending from the spike 11 to the needle is filled with the premedication (first priming step). Next, the needle is inserted into the vein of a patient so as to administer the premedication to the patient.

In the case of administering an anti-cancer agent (second liquid) to the patient, first, the pinch clamp 35 is closed to close the third flow channel 30. Next, the handle 41 of the three-way stopcock 40 is switched to the second position that brings the second flow channel 20 and the third flow channel 30 into communication with each other. Next, the lock connector 50 is detached from the cover 80, and then the lock connector 50 is connected to the female connector (the female connector 200 shown in FIGS. 7A and 7B) of a second medical solution bag in which an anti-cancer agent is stored. The cover 80 remains latched to the tube 10a. Next, the drip chamber 32 is pinched and squeezed with the fingers so as to cause the air within the second flow channel 20 to flow into the second medical solution bag, and when the drip chamber 32 is elastically restored to its original shape, the anti-cancer agent is introduced into the second flow channel 20 from the second medical solution bag. This operation is repeated as needed until the second flow channel 20 is filled with the anti-cancer agent (second priming step). After that, the pinch clamp 35 is opened so as to open the third flow channel 30 to administer the anti-cancer agent to the patient. The flow rate of the anti-cancer agent can be visually checked at the drip chamber 32, and adjusted by using the roller clip 33.

In the case of replacing the second medical solution bag that has run out of the stored anti-cancer agent with a new second medical solution bag, first, the handle 41 of the three-way stopcock 40 is switched to the first position that brings the first flow channel 10 and the third flow channel 30 into communication with each other. Next, the lock connector 50 is disconnected from the female connector of the old second medical solution bag, and then connected to the female connector of the new second medical solution bag. After that, the handle 41 of the three-way stopcock 40 is switched to the second position that brings the second flow channel 20 and the third flow channel 30 into communication with each other so as to restart the administration of the anti-cancer agent. If air flows into the second flow channel 20 extending from the lock connector 50 to the three-way stopcock 40, the pinch clamp 35 is closed, and the same priming operation as described above is performed for the anti-cancer agent of the new second medical solution bag.

When the administration of the anti-cancer agent ends, the handle 41 of the three-way stopcock 40 is first switched to the first position that brings the first flow channel 10 and the third flow channel 30 into communication with each other. Next, the pinch clamp 35 is closed to close the third flow channel 30. Next, the spike 11 is pulled out from the port of the first medical solution bag in which a premedication is stored, and connected to a port of a physiological saline solution bag in which a physiological saline solution is stored. After that, the pinch clamp 35 is opened so as to open the third flow channel 30, whereby the anti-cancer agent remaining in the flow channel extending from the three-way stopcock 40 to the needle inserted in the patient is forced out of the flow channel by the physiological saline solution and administered to the patient.

As described above, the infusion set 1 of the present embodiment includes the three-way stopcock 40 that can perform switching between a state in which the first flow channel 10 and the third flow channel 30 are in communication with each other and a state in which the second flow channel 20 and the third flow channel 30 are in communication with each other, and it is therefore possible to perform a priming operation (first priming step) of introducing a premedication through the spike 11 into the first flow channel 10 and the third flow channel 30 in the state in which the first flow channel 10 and the third flow channel 30 are in communication with each other. The premedication is less hazardous, and thus no problem occurs if the premedication leaks from the needle that is to be inserted into a patient during the first priming step. After that, a priming operation (second priming step) of introducing an anti-cancer agent into the second flow channel 20 through the lock connector 50 is performed by switching the handle 41 so as to bring the second flow channel 20 and the third flow channel 30 into communication with each other. By performing the second priming step after closing the third flow channel 30 with the pinch clamp 35, it is possible to exclude the possibility of the anti-cancer agent leaking out to the external environment during the second priming step. Accordingly, the infusion set 1 of the present embodiment has a high level of safety in that the possibility of a medical solution leaking out to the external environment during a priming operation is reduced.

The third flow channel 30 is provided with the drip chamber 32 and the pinch clamp 35 in this order from the side where the three-way stopcock 40 is provided. Accordingly, as described above, the priming operation of introducing an anti-cancer agent into the second flow channel 20, which is performed before the anti-cancer agent is administered to the patient, can be performed subsequent to the administration of a premedication while the infusion set 1 remains in communication with the patient and the spike 11 remains in connection with the first medical solution bag in which the premedication was stored.

The infusion set 1 includes the three-way stopcock 40 that does not bring the second flow channel 20 into communication with the first flow channel 10 and the third flow channel 30 when the handle 41 is set to the first position, and does not bring the first flow channel 10 into communication with the second flow channel 20 and the third flow channel 30 when the handle 41 is set to the second position. This configuration prevents, for example, a situation in which, during administration of a premedication to the patient, an anti-cancer agent is simultaneously administered together with the premedication, or a situation in which, during administration of an anti-cancer agent to the patient, a premedication is simultaneously administered together with the anti-cancer agent. This is advantageous in, for example, correctly managing the flow rate of the anti-cancer agent by using the drip chamber 32.

Figure 13:
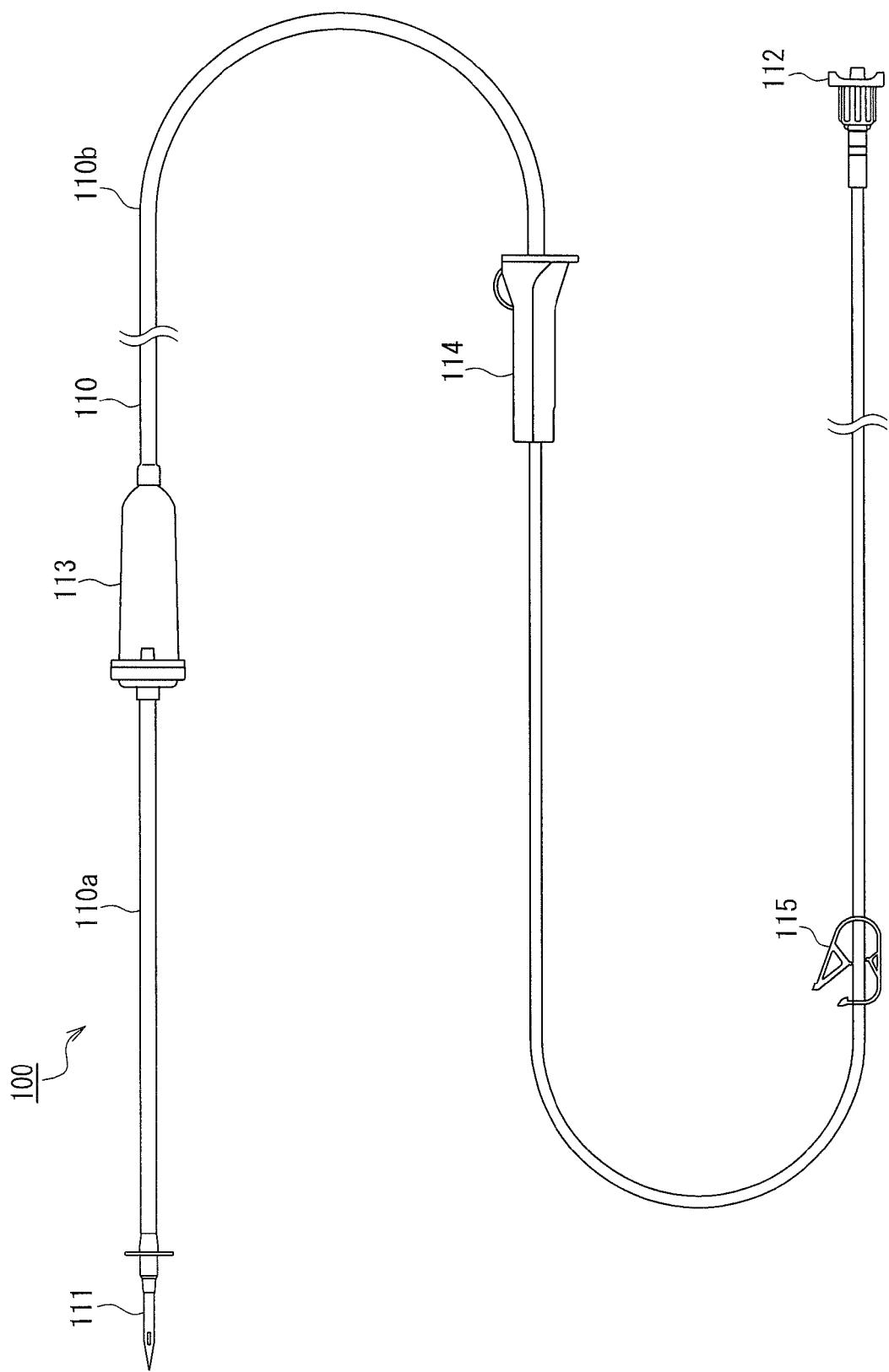
FIG. 13 is a diagram showing an example of a conventional infusion set.

In the infusion set 1 of the present embodiment, the three flow channels 10, 20 and 30 are connected in a T shape or a Y shape via the three-way stopcock 40. As compared with the conventional infusion set 100 shown in FIG. 13 including a single flow channel, the number of flow channels (or in other words, tubes) included in the infusion set 1 is greater, and thus the handling of the infusion set 1 may be troublesome. However, when the second flow channel 20 is not in use, as shown in FIG. 1, the lock connector 50 connected to the upstream end of the second flow channel 20 can be latched to a tube (the tube 10a, 30a, 30b or 30c) constituting the first flow channel 10 or the third flow channel 30 by using the cover 80. Accordingly, the tube 20a constituting the second flow channel 20 or the lock connector 50 will not interfere with, for example, the operation of administering a premedication to the patient. This is advantageous in improving the operational efficiency.

The pair of arms 84 that are provided on the cover 80 and serve as a latch structure include the pair of latch portions 84b that face each other with the spacing W2 therebetween, the spacing W2 being smaller than the outer diameter D of the tube, and thus after a tube has been fitted in between the pair of arms 84, the tube will not fall out from between the pair of latch portions 84b by vibrations, a slight external force or the like. Accordingly, the cover 80 can be latched to the tube in a stable manner.

Furthermore, the pair of inclined surfaces 84a are provided on the tip side of the pair of arms 84, and thus when latching the cover 80 to a tube, the pair of inclined surfaces 84a function as a guide surface that guides the tube between the pair of arms 84. Accordingly, the operation of latching the cover 80 to a tube is facilitated.

In the infusion set 1 of the present embodiment, the lock connector 50, which is connected to the second medical solution bag in which an anti-cancer agent is stored, includes the shield 70 that covers at least the tip of the male luer 51. Accordingly, it is possible to prevent the anti-cancer agent from leaking out from the transverse hole 51h of the male luer 51 to the external environment after the lock connector 50 has been disconnected from the female connector 200.

In a state in which the outer circumferential wall 75 of the shield 70 is not compressed or deformed, a portion in the vicinity of the tip of the male luer 51 including the transverse hole 51h of the male luer 51 is housed in the inner cavity 71c formed in the head portion 71 of the shield 70. At this time, the inner circumferential surface of the inner cavity 71c comes into close contact with the outer circumferential surface of the male luer 51 to close the opening forming the transverse hole 51h. This improves the liquid-tight seal of the transverse hole 51h, and thus the possibility of the anti-cancer agent leaking into the shield 70 through the transverse hole 51h can be reduced. Accordingly, even if the slit 72 of the shield 70 fails to be sealed in a liquid tight manner, the possibility of the anti-cancer agent leaking out of the shield 70 is reduced.

The transverse hole 51h extends in a direction perpendicular to the central axis 51a, and has an opening in the outer circumferential surface of the male luer 51. This is advantageous in closing the transverse hole 51h in a liquid tight manner by the inner circumferential surface of the inner cavity 71c of the shield 70. Also, when the male luer 51 that has passed through the septum 210 is later pulled out from the septum 210, the anti-cancer agent adhering to the periphery of the transverse hole 51h easily can be removed by the end edge of the slit 211 of the septum 210 and the end edge of the slit 72 of the shield 70, and it is therefore possible to reduce the amount of anti-cancer agent remaining in the periphery of the opening forming the transverse hole 51h after disconnection of the lock connector 50 from the female connector 200.

The projection portion 73 protruding toward the female connector 200 is formed on the surface of the head portion 71 that faces the female connector 200. Accordingly, during the period after connection of the lock connector 50 to the female connector 200 until the tip 51t of the male luer 51 is housed in the inner cavity 71c of the shield 70 as a result of the male luer 51 being pulled out from the septum 210, the vicinity portion of the slit 72 of the projection portion 73 of the shield 70 remains in close contact with the septum 210. This is advantageous in reducing the amount of anti-cancer agent adhering to the outer surface of the head portion 71 and the outer surface of the septum 210 after disconnection of the lock connector 50 from the female connector 200.

The projection portion 73 protruding from the head portion 71 of the shield 70 has a substantially mushroom shape including the neck portion 74. As shown in FIG. 10, when the male luer 51 passes through the septum 210, the end edge of the opening 232 of the cap 230 is fitted into the neck portion 74. Accordingly, during the process of pulling out the male luer 51 in the state shown in FIG. 10 from the septum 210, the cap 230 anchors the projection portion 73 such that the septum 210 and the projection portion 73 do not separate from each other. This is advantageous in extending the compressed and deformed shield 70 to its initial state. Also, the septum 210 and the projection portion 73 separate from each other after the male luer 51 has been pulled out of the slit 72 of the head portion 71, and thus the amount of anti-cancer agent remaining on the surfaces of the septum 210 and the projection portion 73 is reduced.

As described above, the lock connector 50 of the present invention includes the shield 70, and thus the possibility of the anti-cancer agent leaking out to the external environment in a state in which the lock connector 50 is not connected to the female connector 200 is reduced. For example, in the case of connecting the lock connector 50 to a new second medical solution bag in place of an empty second medical solution bag, the male luer 51 is covered with the shield 70 immediately after the lock connector 50 is disconnected from the old empty second medical solution bag. In addition, almost no anti-cancer agent remains on the outer surface of the shield 70 or the outer surface of the septum 210 of the female connector 200 of the old second medical solution bag that has been disconnected. This further improves safety.

The infusion set 1 of the present embodiment includes the cover 80 that can be attached to the hood 52 of the lock connector 50. Accordingly, for example, in the case of discarding the infusion set 1 after use, because the shield 70 is covered with the cover 80 by attaching the cover 80 to the lock connector 50, even if the anti-cancer agent adheres to the outer surface of the shield 70, the possibility of the operator accidentally touching the anti-cancer agent is reduced. The possibility of the operator inhaling the vapor of the anti-cancer agent adhering to the outer surface of the shield 70 also is reduced.

The cover 80 includes an engagement structure (the pair of arms 84) that can be latched to a tube constituting the first flow channel 10 or the third flow channel 30. Accordingly, the cover 80 remains latched to the tube even after the cover 80 has been detached from the lock connector 50. It is thereby possible to reduce the possibility of the cover 80 being lost.

Because the cover 80 covers a portion (the shield 70 and the male luer 51 housed in the shield 70) of the lock connector 50 that is to be brought into contact with the female connector 200, the portion of the infusion set 1 can be kept clean before use.

The lock connector 50 includes the lock lever 60 and the hood 52 that serve as a lock mechanism that engages with the female connector 200. With this configuration, the connected state of the lock connector 50 and the female connector 200 is maintained without being unintentionally disconnected by application of vibrations or an external force. It is therefore possible to avoid the risk of the anti-cancer agent leaking out to the external environment as a result of the lock connector 50 and the female connector 200 connected to each other being unintentionally disconnected.

The operation of disengaging the lock connector 50 from the female connector 200 can be performed by simply operating one operation arm 65. For example, the locked state established by the lock mechanism can be released by holding the hood 52 with one hand and then operating the operation arm 65 with one finger (for example, the thumb or the index finger) of the hand. The operation of releasing the locked state established by the lock mechanism is thereby simplified, and thus good operability is provided. For example, the operation of connecting the lock connector 50 sequentially to a plurality of medical solution bags can be performed efficiently.

The inclined surface 64a is formed on a side of the hook 64 opposite to the base 59. Accordingly, during the operation of connecting the lock connector 50 to the female connector 200, the operator does not have to touch the lock lever 60 with his/her hand, and by simply pressing the female connector 200 into the hood 52, the hook 64 and the annular protrusion 223 can be engaged. Therefore, good connection operability is provided.

The hood 52 surrounds the shield 70, and thus the possibility of the operator accidentally touching the shield 70 with his/her hand is reduced. This is advantageous in keeping the operator apart from the anti-cancer agent.

The embodiment described above is merely an example. The present invention is not limited to the embodiment described above, and can be changed as appropriate.

The configuration of the infusion set shown in the embodiment described above may be changed as desired. For example, it possible to provide a co-infusion port (see, for example, Patent Documents 1 and 2) to any one of the first flow channel 10, the second flow channel 20 and the third flow channel 30, in order to blend another medical solution to the medical solution flowing through the flow channel or to extract the medical solution flowing through the flow channel. It is also possible to change the order in which the drip chamber 32, the roller clip 33, the filter 34 and the pinch clamp 35 are disposed in the third flow channel 30. However, in order to facilitate the priming operation, the drip chamber 32 preferably is disposed further upstream (the three-way stopcock 40 direction) than the pinch clamp 35 is. The filter 34 may be omitted. The pinch clamp 35 may be omitted if the roller clip 33 can perform the function of the pinch clamp 35.

The number of tubes constituting each of the first flow channel 10, the second flow channel 20 and the third flow channel 30 is not limited to that of the embodiment described above, and can be changed.

The configuration of the lock connector 50 is not limited to the embodiment described above, and can be changed as appropriate.

The shape of the lock lever 60 can be changed as desired as long as the lock lever 60 includes a hook that can engage with the female connector, and the hook is capable of being elastically displaced. For example, the lock lever 60 of the embodiment described above is formed by forming a substantially U-shaped slit 53 in the hood 52, but the lock lever may be provided, for example, on the outside (on the side away from the male luer 51) of the hood 52 so as to be spaced apart from the hood 52. In this case, the fixed end of the lock lever can be provided on the outer circumferential surface of the hood 52, or the base 59 extending from the hood 52. The hook of the lock lever can be brought into engagement with the female connector via an opening formed in the hood or on an upper side of the upper end edge of the hood.

In the embodiment described above, the hook 64 is engaged with the annular protrusion 223 of the female connector 200, but the portion of the female connector with which the hook 64 is engaged may be changed as appropriate according to the configuration of the female connector. The shape and position of the hook 64 can be changed according to the portion of the female connector with which the hook 64 is engaged.

The shape of the operation arm 65 also can be changed as desired. The force F required to displace the lock lever 60 can be reduced by providing the operating portion 65a of the operation arm 65 below the fixed end 60b of the lock lever 60 in the up-down direction so as to be further away from the fixed end 60b. It is preferable that the proximal end 65b of the operation arm 65 is provided at a position away from the fixed end 60b such that a region in the lock lever 60 between the proximal end 65b and the fixed end 60b can be secured as the elastic portion 61. However, if the proximal end 65b is too close to the free end 60a, it is necessary to make the operation arm 65 longer, which reduces the mechanical strength of the operation arm 65. Generally, as in the embodiment described above, it is preferable to provide the proximal end 65b of the operation arm 65 at a substantially intermediate position between the fixed end 60b and the free end 60a.

The configuration of the lock mechanism of the lock connector is not limited to that of the embodiment described above. For example, the lock connector may include a plurality of lock levers each having a hook that is brought into engagement with the female connector. The lock lever does not need to have a cantilevered support structure as described in the embodiment above, and may have a seesaw structure that swings about a swing shaft provided at a substantially central position in the lengthwise direction of the lock lever (see, for example, Patent Document 3).

In the embodiment described above, the transverse hole 51h of the male luer 51 extends along a straight line perpendicular to the central axis 51a (or in other words, along the radial direction), but the present invention is not limited thereto. The transverse hole 51h may extend along a straight line that intersects with the central axis 51a at an angle other than the right angle. The number of transverse holes 51h is not limited to that of the embodiment described above, and can be changed as desired. Instead of forming the transverse hole 51h, the flow channel 51p may have an opening at the tip surface 51t of the male luer 51.

The configuration of the shield that covers the tip of the male luer of the lock connector is not limited to that shown in the embodiment described above.

For example, the shape of the projection portion 73 protruding from the tip of the head portion 71 can be changed as appropriate. The projection portion 73 may be omitted.

The shape of the outer circumferential wall 75 is not limited to that shown in the embodiment described above as long as it can be elastically compressed and deformed. The outer circumferential wall 75 may have, for example, an ordinary bellows shape. The cross-sectional shape of the outer circumferential wall 75 along a plane vertical to the lengthwise direction of the male luer is not limited to a circle, and may be an equilateral polygon such as a regular square or a regular hexagon, an arbitrary polygon, ellipse, or the like. However, from the viewpoint of preventing buckling distortion of the outer circumferential wall, the cross-sectional shape of the outer circumferential wall 75 is preferably a circle.

In the lock connector, the shield that covers the tip of the male member may be omitted.

In the embodiment described above, a so-called needleless port including a septum 210 is used as the female connector, but the lock connector included in the infusion set of the present invention may be configured to be capable of being connected to a female connector other than the needleless port. For example, the female connector may include a rubber stopper in which a slit-shaped through hole is not formed in advance. In this case, the male luer 51 as the male member is replaced by a resin spike having a sharp tip. The lock mechanism of the lock connector is changed as appropriate according to the shape of the female connector.

The latch structure for latching the lock connector to a tube may be provided onto the bottom plate 82, rather than the outer wall 81 of the cover 80. The latch structure is not limited to the pair of arms 84 shown in the embodiment described above, and can be changed into an arbitrary shape. For example, the latch structure may be constituted by one arm that has a substantially J shape or a substantially L shape so as to be capable of being latched to a tube.

In the embodiment described above, the lock connector is latched indirectly to a tube via the cover by providing the latch structure to the cover, but the lock connector may be latched directly to a tube by providing the latch structure to the lock connector itself.

The infusion set of the present invention does not necessarily have the latch structure for latching the lock connector to a tube.

The cover that covers a portion of the lock connector, the portion being connected to the female connector, may be omitted.

In the embodiment described above, an example was described in which a premedication is stored in the first medical solution bag to which the spike 11 is connected, and an anti-cancer agent is stored in the second medical solution bag to which the lock connector 50 is connected, but the types of liquids stored in the first medical solution bag and the second medical solution bag to which the infusion set of the present invention is connected are not limited thereto. The liquids may be an arbitrary medical solution and a liquid other than medical solutions such as a physiological saline solution, a nutritional solution such as a dextrose solution, blood, and the like.

In the embodiment described above, an example was described in which the hazardous drug is an anti-cancer agent, but the present invention is equally applicable to a hazardous drug other than the anti-cancer agent.

INDUSTRIAL APPLICABILITY

The present invention preferably is used as an infusion set used in the field of medicine when administering a liquid to a patient. In particular, the present invention is preferably used as an infusion set for administering, to a patient, a medical solution containing a hazardous drug whose leakage to the external environment needs to be prevented, such as an anti-cancer agent.

DESCRIPTION OF REFERENCE SIGNS

1 Infusion Set
10 First Flow Channel
10a Tube Constituting First Flow Channel
11 Spike
20 Second Flow Channel
20a Tube Constituting Second Flow Channel
30 Third Flow Channel
30a, 30b, 30c Tube Constituting Third Flow Channel
31 Male Connector
32 Drip chamber
35 Pinch clamp
40 Three-Way Stopcock
41 Handle
50 Lock Connector
51 Male Luer (Male Member)

51h Transverse Hole
51p Flow Channel
60 Lock Lever (Lock Mechanism)
65 Operation Arm
70 Shield
71 Head Portion of Shield
71c Inner Cavity
73 Projection Portion
75 Outer Circumferential Wall of Shield
80 Cover
84 Arm (Latch Structure)

The invention claimed is:

1. An infusion set comprising:
a first flow channel that is constituted by a pliable tube and includes a spike provided at one end thereof;
a second flow channel that is constituted by a pliable tube and includes a lock connector provided at one end thereof, the lock connector including a lock mechanism that is brought into engagement with a female connector;
a third flow channel that is constituted by a pliable tube and includes a male connector provided at one end thereof; and
a three-way stopcock to which another end of the first flow channel, another end of the second flow channel and another end of the third flow channel are connected,
wherein the three-way stopcock includes a handle that can be switched between a first position and a second position, the first position being a position that brings the first flow channel and the third flow channel into communication with each other, and the second position being a position that brings the second flow channel and the third flow channel into communication with each other.

2. The infusion set according to claim 1,
wherein the second flow channel is not in communication with the first flow channel and the third flow channel when the handle is set to the first position, and the first flow channel is not in communication with the second flow channel and the third flow channel when the handle is set to the second position.

3. The infusion set according to claim 1 or 2,
wherein the third flow channel is provided with a drip chamber and a pinch clamp for opening and closing the third flow channel in this order from a side where the three-way stopcock is provided.

4. The infusion set according to claim 1, further comprising
a cover that covers a portion of the lock connector, the portion being connected to the female connector, and that can be attached to and detached from the lock connector.

5. The infusion set according to claim 1, further comprising
a latch structure that allows the lock connector to be latched directly or indirectly to the tube constituting the first flow channel or the tube constituting the third flow channel.

6. The infusion set according to claim 1,
wherein the lock connector includes a rod-shaped male member including a flow channel through which a liquid flows, and a shield that covers at least a tip of the male member,
wherein the shield includes an outer circumferential wall that has a substantially cylindrical shape and is capable of being elastically compressed and deformed in a lengthwise direction of the male member, and a head portion that is provided at one end of the outer circumferential wall and through which the male member passes when the outer circumferential wall is compressed and deformed.

7. The infusion set according to claim 6,
wherein a transverse hole in communication with the flow channel has an opening in an outer circumferential surface of the male member in a vicinity of the tip of the male member,
an inner cavity in which the tip of the male member is housed is provided in the head portion, and
in a state in which the outer circumferential wall is not compressed or deformed, an inner circumferential surface of the inner cavity comes into close contact with the outer circumferential surface of the male member so as to close the opening of the transverse hole.

8. The infusion set according to claim 6 or 7,
wherein a protruding projection portion is provided at a tip position of the head portion through which the male member passes.

9. The infusion set according to claim 1,
wherein the lock connector includes only one operation arm for performing an operation of disengaging the engagement of the lock mechanism with the female connector.

10. A method for using the infusion set according to claim 1, the method comprising:
a first priming step of introducing a first liquid through the spike into the first flow channel and the third flow channel in a state in which the handle is set to the first position;
a first liquid administering step of administering the first liquid to a patient;
a second priming step of introducing a second liquid through the lock connector into the second flow channel by switching the handle to the second position; and
a second liquid administering step of administering the second liquid to the patient.

11. The method for using the infusion set according to claim 10,
wherein the second priming step is performed in a state in which the third flow channel is closed.

12. The method for using the infusion set according to claim 10,
wherein the first liquid does not contain a hazardous drug, but the second liquid contains a hazardous drug.

* * * * *